(12) United States Patent
Wada

(10) Patent No.: US 10,672,127 B2
(45) Date of Patent: Jun. 2, 2020

(54) INFORMATION PROCESSING APPARATUS, INFORMATION PROCESSING METHOD, AND PROGRAM

(71) Applicant: CANON KABUSHIKI KAISHA, Tokyo (JP)

(72) Inventor: Manabu Wada, Tokyo (JP)

(73) Assignee: CANON KABUSHIKI KAISHA, Tokyo (JP)

( * ) Notice: Subject to any disclaimer, the term of this patent is extended or adjusted under 35 U.S.C. 154(b) by 88 days.

(21) Appl. No.: 15/797,311

(22) Filed: Oct. 30, 2017

(65) Prior Publication Data

US 2018/0122077 A1 May 3, 2018

(30) Foreign Application Priority Data

Oct. 31, 2016 (JP) .................. 2016-213422

(51) Int. Cl.
| | | |
|---|---|---|
| G06K 9/00 | (2006.01) |
| G06T 7/00 | (2017.01) |
| G06T 5/00 | (2006.01) |
| G06T 7/246 | (2017.01) |
| A61B 3/00 | (2006.01) |
| A61B 3/10 | (2006.01) |
| A61B 3/12 | (2006.01) |

(52) U.S. Cl.
CPC .......... *G06T 7/0016* (2013.01); *A61B 3/0025* (2013.01); *A61B 3/102* (2013.01); *A61B 3/1233* (2013.01); *G06T 5/002* (2013.01); *G06T 7/248* (2017.01); *G06T 2207/10101* (2013.01); *G06T 2207/30041* (2013.01)

(58) Field of Classification Search
None
See application file for complete search history.

(56) References Cited

U.S. PATENT DOCUMENTS

| | | | |
|---|---|---|---|
| 8,433,393 B2 * | 4/2013 | Sharma | A61B 3/102 600/477 |
| 9,700,206 B2 * | 7/2017 | An | A61B 3/1233 |
| 10,402,965 B1 * | 9/2019 | Bagherinia | G06T 7/0081 |
| 2008/0025570 A1 * | 1/2008 | Fingler | A61B 3/102 382/107 |
| 2014/0221827 A1 | 8/2014 | Motaghiannezam | |
| 2015/0257850 A1 * | 9/2015 | Sakamoto | G06T 7/12 600/424 |
| 2015/0374227 A1 * | 12/2015 | Takeno | A61B 3/102 600/425 |
| 2016/0227999 A1 * | 8/2016 | An | A61B 3/1233 |
| 2017/0024910 A1 * | 1/2017 | Griffin | G06T 11/003 |
| 2017/0035286 A1 * | 2/2017 | Meyer | A61B 3/102 |
| 2017/0069105 A1 * | 3/2017 | Kano | A61B 3/102 |
| 2017/0112377 A1 * | 4/2017 | Shiba | A61B 3/1233 |
| 2017/0119242 A1 * | 5/2017 | Jia | A61B 3/0025 |
| 2017/0119244 A1 * | 5/2017 | Shiba | G06T 7/11 |
| 2018/0256024 A1 * | 9/2018 | An | A61B 3/102 |

\* cited by examiner

*Primary Examiner* — Shervin K Nakhjavan
(74) *Attorney, Agent, or Firm* — Canon U.S.A., Inc. IP Division

(57) ABSTRACT

An information processing apparatus includes a determination unit configured to determine, as a threshold value to which a signal intensity value corresponding to a shadow region is compared, a value different from a threshold value to which a signal intensity value corresponding to a region other than the shadow region is compared.

33 Claims, 12 Drawing Sheets

INFORMATION PROCESSING APPARATUS, INFORMATION PROCESSING METHOD, AND PROGRAM

BACKGROUND

Field of the Disclosure

The present disclosure relates to information processing apparatuses, information processing methods, and programs.

Description of the Related Art

Angiography methods using optical coherence tomography (hereinafter, "OCT") without a contrast agent have been discussed. Such angiography methods are called "OCT angiography" (hereinafter, "OCTA"), and OCTA images acquired by OCTA are images of motion contrast values. As used herein, the term "motion contrast value" refers to a value obtained ideally by repeatedly capturing images of the same cross section and detecting temporal changes in a subject between the plurality of images of the cross-section.

United States Patent Application No. 2014/221827 discusses threshold value processing as a method for reducing noise in OCTA images. In the threshold value processing, an intensity value of a complex OCT signal is compared to a threshold value, and if the intensity value of the complex OCT signal is lower than the threshold value, a corresponding motion contrast value is set to zero. In the method discussed in United States Patent Application No. 2014/221827, a value that is 10 dB above the mean value of the noise floor is used as the threshold value.

SUMMARY

According to an aspect of the present invention, an information processing apparatus includes a first acquisition unit configured to acquire a plurality of pieces of tomographic data each of which indicating indicates a cross section of an eye fundus and is acquired based on the basis of measurement light which is controlled so that the same position of the eye fundus is scanned, an identification unit configured to identify a shadow region in at least one of the plurality of pieces of tomographic data, a determination unit configured to determine, in a case where a shadow region is identified by the identification unit, a value different from a threshold value to which a signal intensity value corresponding to a region other than the shadow region is compared, as a threshold value to which a signal intensity value corresponding to the shadow region is compared, a comparison unit configured to compare to the threshold value to a signal intensity value acquired from at least one of the plurality of pieces of tomographic data, a second acquisition unit configured to acquire a motion contrast value from a result of the comparison performed by the comparison unit and the plurality of pieces of tomographic data, and a generation unit configured to generate a motion contrast image based on the motion contrast value acquired by the second acquisition unit.

Further features of the present invention will become apparent from the following description of exemplary embodiments with reference to the attached drawings.

DESCRIPTION OF THE EMBODIMENTS

In a case in which tomographic data acquired by optical coherence tomography (OCT) contains a shadow region formed by a shielding object which prevents measurement light from entering a retina, the shadow region has a lower signal intensity than the signal intensity of a region with no shadow. Thus, if a threshold value is uniformly set, even when the shadow region contains tissue or the like to be imaged, a motion contrast value corresponding to the shadow region is set to zero by the above-described threshold value processing. Consequently, the tissue may not be imaged.

The present disclosure is directed to a technique for imaging shadow regions as appropriate.

The present disclosure is directed not only to the above-described technique but also to a technique for producing an advantage that is derived from a configuration illustrated in an exemplary embodiment of the present invention described below and cannot be produced by a conventional technique.

Various exemplary embodiments of the invention will be described below with reference to the drawings. It should be noted that configurations described in the exemplary embodiments are mere examples and the scope of the invention is not limited to the illustrated configurations.

Figure 1:
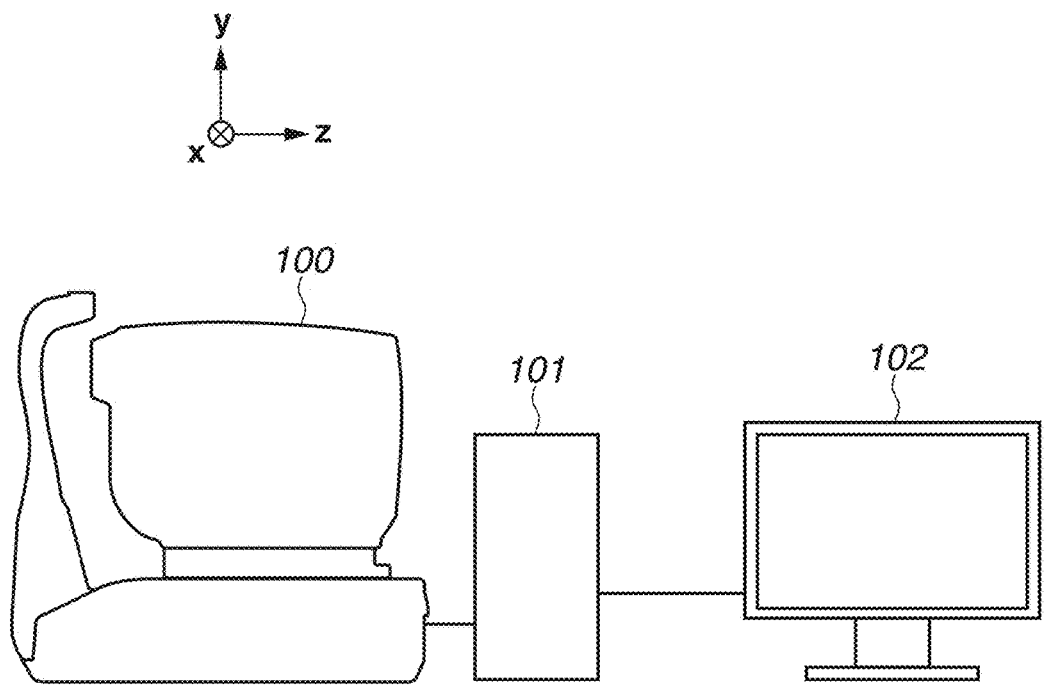
FIG. 1 illustrates an example of the configuration of an optical coherence tomographic imaging apparatus.

A first exemplary embodiment will be described below. FIG. 1 illustrates an example of the configuration of an optical coherence tomographic imaging apparatus. The optical coherence tomographic imaging apparatus includes a data acquisition unit 100, a signal processing unit 101, and a display unit 102. While the data acquisition unit 100, the signal processing unit 101, and the display unit 102 are separated in FIG. 1, the data acquisition unit 100 can include at least one of the signal processing unit 101 and the display unit 102.

The data acquisition unit 100 is an OCT device which scans measurement light over an eye to be examined and captures images of the eye to acquire tomographic data. The signal processing unit 101 is an information processing apparatus which generates OCTA images of the eye to be examined from the tomographic data acquired by the data acquisition unit 100. The display unit 102 is a display which displays the OCTA images of the eye generated by the signal processing unit 101. The configurations of the data acquisition unit 100, the signal processing unit 101, and the display unit 102 will be described below.

First, the configuration of the data acquisition unit 100 will be described below.

Figure 2:
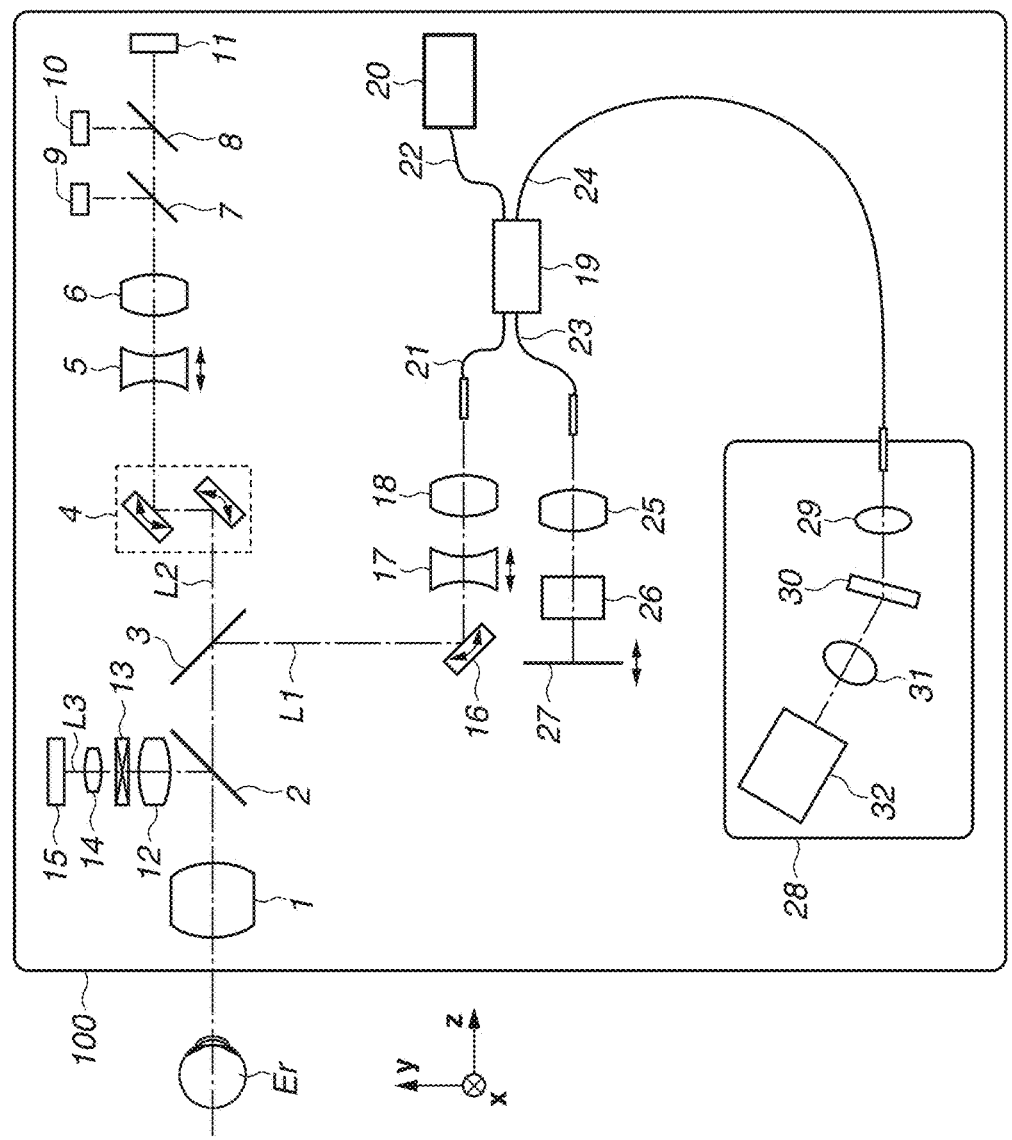
FIG. 2 illustrates an example of the configuration of a data acquisition unit.

FIG. 2 illustrates an example of the configuration of the data acquisition unit 100. An optical system illustrated in FIG. 2 includes an OCT optical system for acquiring tomographic data on the eye fundus and a scanning laser ophthalmoscopic (SLO) optical system for acquiring images of the surface of the eye fundus.

An objective lens 1 is situated to face an eye-to-be-examined Er, and a first dichroic mirror 2 and a second dichroic mirror 3 are situated on an optical path of the objective lens 1. The first dichroic mirror 2 and the second dichroic mirror 3 split light according to wavelength bands into an optical path L1 of the OCT optical system, an optical path L2 of the SLO optical system and a fixation lamp for the observation of the eye-to-be-examined Er, and an optical path L3 for the observation of the anterior eye portion.

On the optical path L2 of the SLO optical system and the fixation lamp, a SLO scan unit 4, lenses 5 and 6, a mirror 7, a third dichroic mirror 8, a photodiode 9, a SLO light source 10, and a fixation lamp 11 are disposed.

The mirror 7 is a prism on which a perforated mirror or hollow mirror is deposited, and separates illumination light emitted from the SLO light source 10 and return light from the eye to be examined Er. The third dichroic mirror 8 splits light into optical paths to the SLO light source 10 and the fixation lamp 11 according to wavelength bands.

The SLO scan unit 4 scans light emitted from the SLO light source 10 and the fixation lamp 11 over the eye-to-be-examined Er. The SLO scan unit 4 includes an X-scanner configured to scan light in an X-direction and a Y-scanner configured to scan light in a Y-direction. According to the present exemplary embodiment, the X-scanner needs to scan light at high speed and, thus, includes a polygonal mirror, and the Y-scanner includes a galvanometer mirror.

The lens 5 is driven by a motor (not illustrated) to focus the SLO optical system and the fixation lamp. The SLO light source 10 generates light having a wavelength of around, for example, 780 nm. The numerical value of the wavelength specified in the present specification is a mere example and can be any other value. The photodiode 9 detects return light from the eye-to-be-examined Er. The fixation lamp 11 generates visible light to prompt an examinee to fix the eye movement of the examinee.

Light emitted from the SLO light source 10 is reflected by the third dichroic mirror 8, passes through the mirror 7, the lens 6, and then the lens 5, and is scanned over the eye-to-be-examined Er by the SLO scan unit 4. Return light from the eye-to-be-examined Er returns through the same path as the projection light and is then reflected by the mirror 7 and guided to the photodiode 9.

Light from the fixation lamp 11 passes through the third dichroic mirror 8, the mirror 7, the lens 6, and then the lens 5 and is scanned over the eye-to-be-examined Er by the SLO scan unit 4. At this time, the fixation lamp 11 blinks in response to the movement of the SLO scan unit 4 so that a predetermined shape is formed at a predetermined position on the eye-to-be-examined Er to prompt the examinee to fix the eye movement of the examinee.

On the optical path L3 for the observation of the anterior eye portion, a lens 12, a split prism 13, a lens 14, and a charge-coupled device (CCD) 15 for the observation of the anterior eye portion are disposed. The CCD 15 has sensitivity around the wavelength of a light source (not illustrated) for the observation of the anterior eye portion, for example, around 970 nm.

The split prism 13 is situated in a conjugate position to the pupil of the eye-to-be-examined Er and is capable of detecting the distance between the eye-to-be-examined Er and the data acquisition unit 100 in a Z-direction (anteroposterior direction) as a split image of the anterior eye portion.

On the optical path L1 of the OCT optical system for capturing image data of the eye-to-be-examined Er are disposed an XY scanner 16 and lenses 17 and 18. The XY scanner 16 is configured to scan light from an OCT light source 20 over the eye-to-be-examined Er. While the XY scanner 16 is illustrated as a single mirror, the XY scanner 16 is a galvanometer mirror configured to scan light in two axial directions of X and Y.

The lens 17 is driven by a motor (not illustrated) and is configured to focus light emitted from an optical fiber 21 and coming from the OCT light source 20 onto the eye-to-be-examined Er. By this focusing, return light from the eye-to-be-examined Er is simultaneously focused in the shape of a spot on a leading edge of the optical fiber 21 and enters the optical fiber 21.

An optical coupler 19, the OCT light source 20, the optical fibers 21 to 24 connected and integrated to the optical coupler 19, a lens 25, a dispersion-compensating glass 26, a reference mirror 27, and a spectroscope 28 are further disposed.

Light emitted from the OCT light source 20 through the optical fiber 22 is divided into measurement light and reference light at the optical coupler 19. The measurement light is emitted toward the eye-to-be-examined Er through an optical fiber 21, the optical path L1 of the OCT optical system, and the objective lens 1. The measurement light emitted toward the eye-to-be-examined Er is reflected and scattered at the eye-to-be-examined Er and travels through the same path to reach the optical coupler 19.

Meanwhile, the reference light is emitted toward the reference mirror 27 through the optical fiber 23, the lens 25, and the dispersion-compensating glass 26. The reference light reflected from the reference mirror 27 travels through the same optical path to reach the optical coupler 19.

The measurement light and the reference light having reached the optical coupler 19 as described above are combined into interference light. Interference occurs when the optical path lengths of the measurement light and the reference light are substantially the same. The reference mirror 27 is held such that the reference mirror 27 is adjustable in an optical axis direction by a motor (not illustrated) and a driving mechanism, so the optical path length of the reference light is adjustable to the optical path length of the measurement light which changes according to the eye-to-be-examined Er. The interference light is guided to the spectroscope 28 through the optical fiber 24.

The spectroscope 28 includes lenses 29 and 31, a grating 30, and a line sensor 32. Interference light emitted from the optical fiber 24 is changed into parallel light through the lens 29, dispersed by the grating 30, and focused on the line sensor 32 by the lens 31.

While a Michelson interference system is used as the interference system according to the present exemplary embodiment, a Mach-Zehnder interference system can be used. It is desirable to use a Mach-Zehnder interference system in a case in which the difference in light quantity between the measurement light and the reference light is large, or a Michelson interference system in a case in which the difference is relatively small.

Next, the configurations of the signal processing unit 101 and the display unit 102 will be described below.

Figure 3:
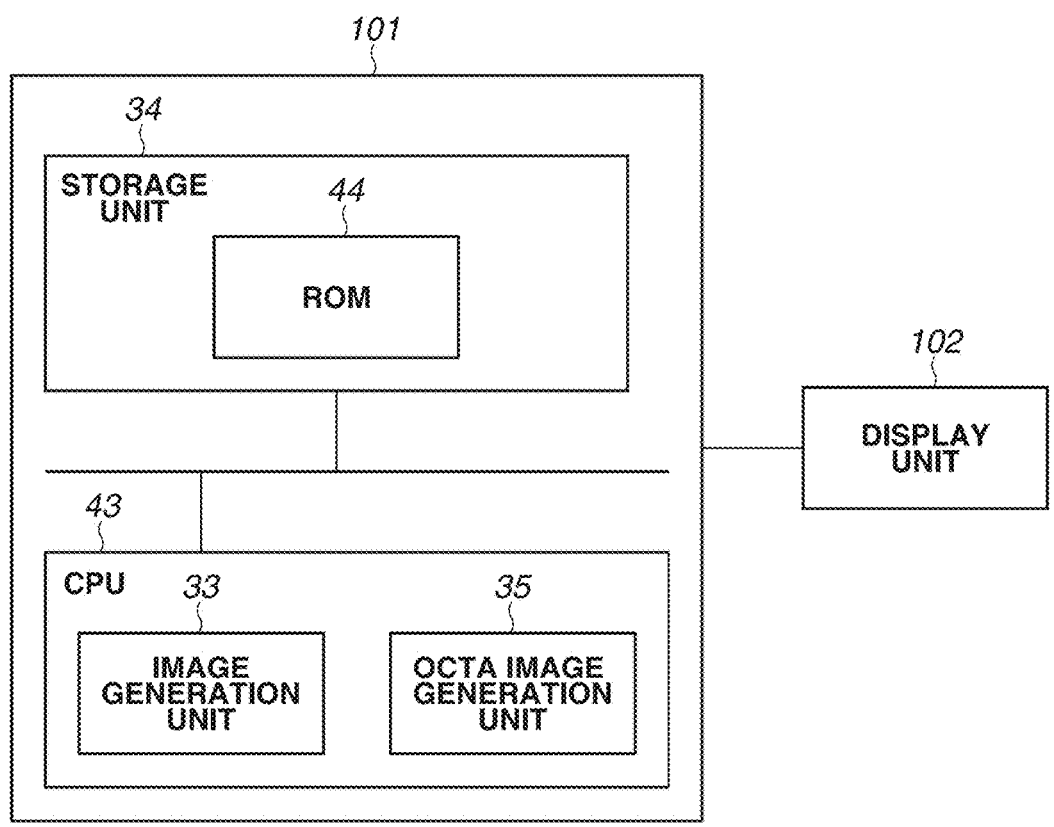
FIG. 3 illustrates an example of the functional configuration of a signal processing unit.

FIG. 3 illustrates an example of the functional configuration of the signal processing unit 101. The signal processing unit 101 includes a storage unit 34 and a central processing unit (CPU) 43. The signal processing unit 101 is, for example, an information processing apparatus such as a personal computer. The storage unit 34 and the CPU 43 are connected to each other for communicating. Further, the storage unit 34 and the CPU 43 are connected to the display unit 102 for communication. The storage unit 34 includes a read-only memory (ROM) 44. The CPU 43 executes a program stored in the ROM 44 to function as an image generation unit 33 and an OCTA image generation unit 35.

The signal processing unit 101 can include a single CPU or a plurality of CPUs and a single ROM or a plurality of ROMs. Specifically, the signal processing unit 101 functions as the above-described units in a case in which at least one or more processors and at least one memory are connected and the at least one or more processors execute a program stored in the at least one or more memories. The processing apparatus is not limited to the CPUs and can be a graphics processing unit (GPU), an application-specific integrated circuit (ASIC), a micro-processing unit (MPU), a field-programmable gate array (FPGA), etc. Further, the concept of "at least one or more processors" includes a CPU including at least one or more cores.

The image generation unit 33 generates various images based on data acquired by the data acquisition unit 100. More specifically, the image generation unit 33 is connected to the photodiode 9 and the line sensor 32 of the data acquisition unit 100 and the storage unit 34 for communication. The image generation unit 33 generates a SLO image from a plurality of pieces of data acquired from the photodiode 9 when the eye-to-be-examined Er is scanned in the X- and Y-directions using the SLO scan unit 4. As used herein, the term "SLO image" refers to a two-dimensional image of the surface of the eye fundus viewed from the anterior eye portion side.

Further, the image generation unit 33 Fourier-transforms interference data acquired from the line sensor 32 and converts the Fourier-transformed data into luminance information or density information to acquire an image of the eye-to-be-examined Er in a depth direction (Z-direction). This scan is referred to as an A-scan, and a tomographic image acquired by the A-scan is referred to as an A-scan image.

A plurality of A-scan images is acquired by A-scans over the eye-to-be-examined Er in a predetermined transverse direction using the XY scanner 16. For example, tomographic images of an XZ-plane are acquired by scans in the X-direction, whereas tomographic images of a YZ-plane are acquired by scans in the Y-direction. This scan over the eye-to-be-examined Er in the predetermined transverse direction is referred to as a B-scan, and a tomographic image acquired by the B-scan is referred to as a B-scan image.

Further, a scan over the XZ- or YZ-plane of the B-scan in a direction that is orthogonal to the XZ- or YZ-plane is referred to as a C-scan, and XYZ three-dimensional tomographic data acquired by the C-scan is referred to as C-scan data.

The storage unit 34 is connected to the image generation unit 33, the OCTA image generation unit 35, and the display unit 102, stores the SLO images and the two- or three-dimensional tomographic data acquired from the image generation unit 33, and stores the two- or three-dimensional OCTA data acquired from the OCTA image generation unit 35.

The OCTA image generation unit 35 is connected to the storage unit 34 and acquires tomographic data from the storage unit 34 to generate an OCTA image (motion contrast image). Details of the OCTA image generation unit 35 will be described below.

The display unit 102 displays the SLO images, tomographic data, and OCTA data stored in the storage unit 34. Examples of the display unit 102 include a liquid crystal display.

The following describes a process of observation and imaging performed by the optical coherence tomographic imaging apparatus including the data acquisition unit 100, the signal processing unit 101, the display unit 102 described above.

Figure 4:
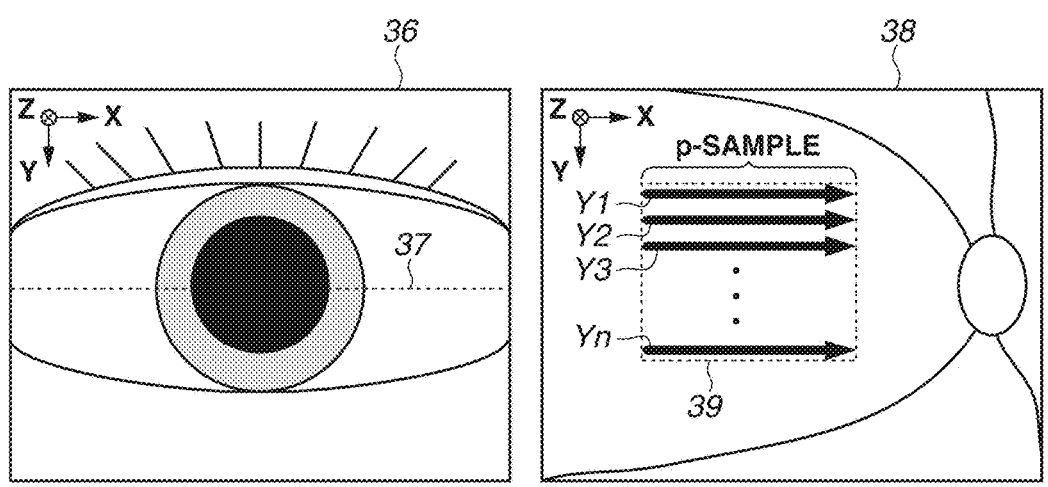
FIG. 4 illustrates an example of an anterior eye portion observation image and a scanning laser ophthalmoscopic (SLO) image displayed on a display unit during observation.

First, the observation will be described below with reference to FIG. 4. FIG. 4 illustrates an example of a screen displayed on the display unit 102 during the observation. In FIG. 4, the display unit 102 displays an anterior eye portion observation image 36 and a SLO image 38. The screen displayed on the display unit 102 during the observation of the eye-to-be-examined Er is not limited to the exemplary screen illustrated in FIG. 4.

After the eye-to-be-examined Er is positioned in front of the objective lens 1, a user aligns the eye-to-be-examined Er with the data acquisition unit 100 in the XYZ-directions using a joystick (not illustrated) while checking the anterior eye portion observation image 36. In the alignment in the XY-directions, for example, the user operates the data acquisition unit 100 to locate the center of the pupil in the anterior eye portion observation image 36 in the center of the screen on which the anterior eye portion observation image 36 is displayed. In the alignment in the Z-direction, for example, the anterior eye portion observation image 36 is split along a dotted line 37 if the alignment is not conducted as appropriate. Thus, the user operates the data acquisition unit 100 not to split the anterior eye portion observation image 36. The alignment can be conducted manually by a user or can be conducted automatically. Further, the alignment can be conducted either manually or automatically. Further, the alignment method is not limited to the above-described method, and any known method can be used.

After the alignment of the eye-to-be-examined Er with the data acquisition unit 100 in the XYZ-directions is completed as described above, the SLO image 38 generated by scans conducted by the SLO scan unit 4 in the XY-directions is displayed on the display unit 102. The timing at which the SLO image 38 is displayed on the display unit 102 is not limited to the timing described above as an example. The anterior eye portion observation image 36 and the SLO image 38 are continually updated so that the user can observe the eye-to-be-examined Er with substantially no delay.

Further, a scan area 39 in the SLO image 38 indicates an area to be scanned during acquisition of OCTA data. The scan area 39 is superimposed on the SLO image 38. The user operates the scan area 39 with a scan position changing unit (not illustrated) such as a mouse or touch panel to set a desired scan position. When the operations described above are completed, the observation is ended.

Next, the imaging will be described below. When the user operates an imaging start button (not illustrated), the data acquisition unit 100 scans the measurement light over the scan area 39. In OCTA, B-scans are repeated so that the same cross-section, i.e., the same position is scanned, and temporal changes in a subject between the B-scans are detected. Thus, in the present exemplary embodiment, B-scans are performed so that the same position are repeatedly scanned m times. In a case of scanning the scan area 39 according to the present exemplary embodiment, B-scans are repeated m times over each of scan positions Y1 to Yn in the Y-direction. However, since the eye-to-be-examined Er moves, it is sometimes impossible to constantly perform scan in a manner such that the same position of the eye fundus is scanned. Further, in a case in which an eye-to-be-examined tracking function is included, it is sometimes impossible to constantly scan the same position of the eye fundus due to imperfection of the tracking function. Specifically, it is not always possible to scan exactly the same position of the eye fundus even with the measurement light which is controlled so that the same position of the eye fundus is scanned by the apparatus. Thus, the term "the same position of the eye fundus" used in the present specification refers not only to exactly the same position of the eye fundus but also to substantially the same position of the eye fundus.

According to the present exemplary embodiment, an A-scan in each B-scan includes p-sample position data in the X-direction, and one A-scan includes q pieces of data in the Z-direction. According to the present exemplary embodiment, the scan area 39 is scanned to acquire n×m B-scans (the number of A-scans is n×m×p, and the total number of data is n×m×p×q) on an XYZ-plane.

After the acquisition of data on the scan area 39 by the data acquisition unit 100 is completed, the image generation unit 33, for example, generates B-scan images from all the acquired data. Specifically, the image generation unit 33 performs background subtraction and Fourier transform on each B-scan. From the Fourier transform, a complex OCT signal including a real and an imaginary part is acquired, so the image generation unit 33 calculates the absolute value of the complex OCT signal to generate B-scan images. Specifically, the data acquisition unit 100 generates an n×m B-scan image. In other words, the data acquisition unit 100 corresponds to an example of a first acquisition unit configured to acquire a plurality of pieces of tomographic data each specifying a cross section of the eye fundus and acquired based on the measurement light which is controlled so that the same position of the eye fundus is scanned.

After the image generation unit 33 generates a B-scan image, the generated B-scan image is stored in the storage unit 34, and the OCTA image generation unit 35 generates an OCTA image. Details of the processing performed by the OCTA image generation unit 35 will be described below. After the OCTA image generation unit 35 generates an OCTA image, the generated OCTA image is stored in the storage unit 34, and the CPU 43 outputs the OCTA image to the display unit 102 to display the OCTA image on the display unit 102. The user checks the OCTA image displayed on the display unit 102 to, for example, determine whether to conduct next imaging. The foregoing is the description of the observation and the imaging.

Next, details of the OCTA image generation unit 35 will be described below.

Figure 5:
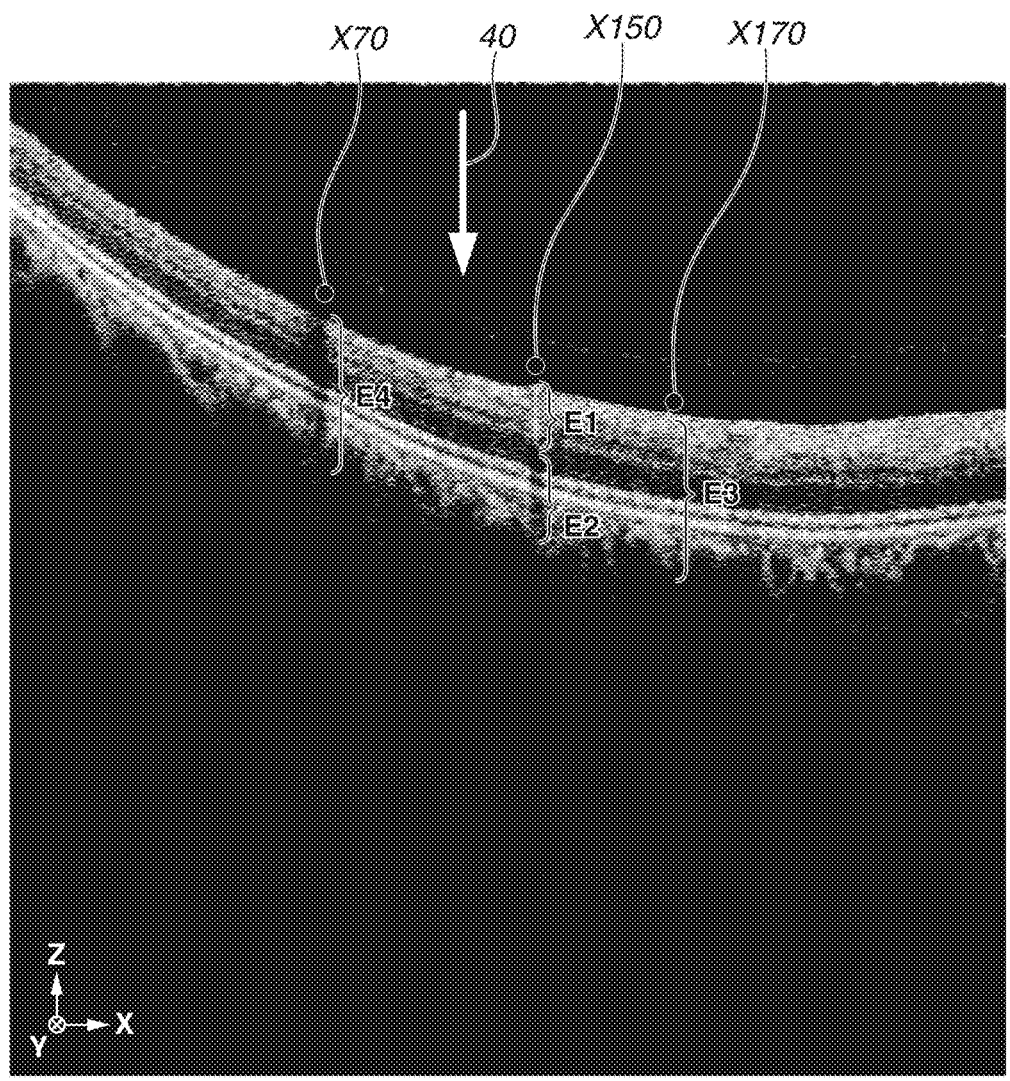
FIG. 5 illustrates an example of a B-scan image of a retina portion in a position in a Y-direction in a scan area.

Prior to the description of the OCTA image generation unit 35, a shadow cast by a shielding object that exists in the eye-to-be-examined Er and prevents the measurement light emitted from the OCT light source 20 from entering the retina will be described below with reference to FIG. 5. FIG. 5 illustrates an example of a B-scan image of the retina portion of the scan area 39 in a position in the Y-direction. An upper part of FIG. 5 is the vitreous body, and the measurement light emitted from the OCT light source 20 enters from the upper part in FIG. 5, so the incident direction of the measurement light is as specified by an arrow 40.

Further, in FIG. 5, X150 indicates a position in the X-direction in a tomographic image in which there is a retinal blood vessel in the incident direction of the measurement light. Further, X170 indicates a position in the X-direction in a tomographic image in which there is no retinal blood vessel in the incident direction of the measurement light, and X70 indicates a position in the X-direction in a tomographic image in which there is vitreous body opacity (not illustrated) in the incident direction of the measurement light.

First, from the tomographic image of the position X150 in the X-direction a retinal blood vessel E1 is observed. In general, the retinal blood vessel E1 is observed as a long, thin highly-reflective object and exists from the ganglion cell layer to the vicinity of the boundary portion between the inner nuclear layer and the outer plexiform layer. When the retinal blood vessel E1 exists, the measurement light is shielded by the retinal blood vessel E1. This prevents the measurement light from reaching the posterior part to cast a shadow E2. The shadow E2 is observed with low luminance on the tomographic image.

Next, from the tomographic image of the position X170 in the X-direction a cross section E3 from the inner limiting membrane to the choroid is observed with no shadow. This is because no shielding object which prevents the measurement light from entering the retina exists in the position X170 in the X-direction in the incident direction of the measurement light.

Further, from the tomographic image of the position X70 in the X-direction it is found that a shadow is cast over a cross section E4 from the inner limiting membrane to the choroid. This is because of the following reason. The opacified vitreous body (not illustrated) exists in the incident direction of the measurement light and blocks the measurement light. This makes it difficult for the measurement light to reach the cross section from the inner limiting membrane to the choroid which exists behind the opacified vitreous body viewed from the incident direction of the measurement light, and a shadow is cast.

As described above, a shadow is cast over the cross section which exists behind the shielding object viewed from the incident direction of the measurement light. Further, it can be said that the position in the Z-direction in which a shadow is cast varies depending on the position of the shielding object in the Z-direction in the eye-to-be-examined Er.

While the position X150 in the X-direction (retinal blood vessel E1) and the position X70 in the X-direction (case in which the opacified vitreous body (not illustrated) exists) are described as examples in which a shadow is cast in the present exemplary embodiment, a shadow is cast also in other cases such as lens opacity, retinal hemorrhage, and hard exudate. In the case of lens opacity, as illustrated in the cross section of the position X170 in the X-direction, a shadow is cast over the cross section from the inner limiting membrane to the choroid. In the cases of retinal hemorrhage, hard exudate, etc., the position of a shadow in the Z-direction varies depending on the position of the retinal hemorrhage or hard exudate in the Z-direction in the cross section from the nerve fiber layer to the choroid.

Figure 6:
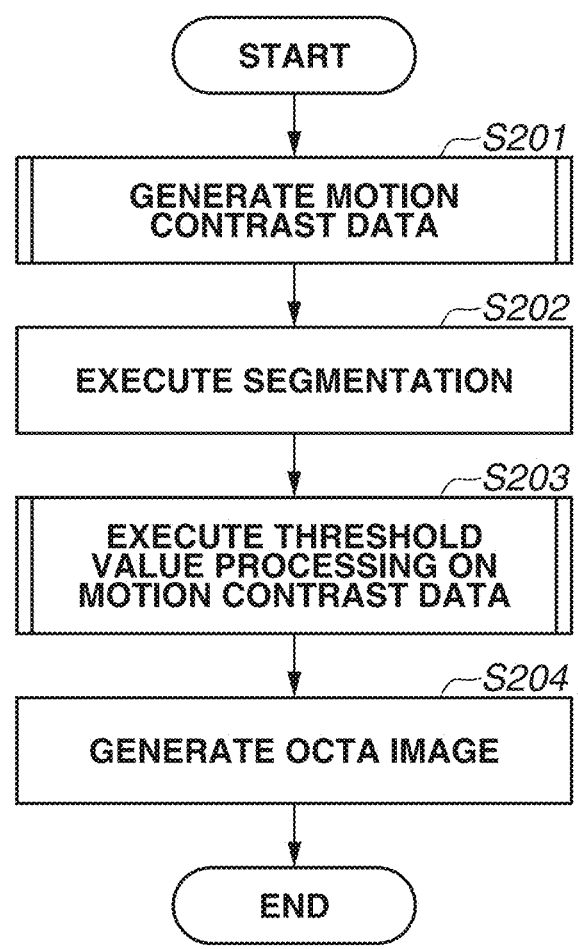
FIG. 6 is a flow chart illustrating an example of a process performed by an optical coherence tomography angiographic (OCTA) image generation unit.

The OCTA image generation unit 35 will be described below with reference to FIG. 6. FIG. 6 is a flow chart illustrating a series of processing performed by the OCTA image generation unit 35 (information processing method).

The following description of the OCTA image generation unit 35 is about the process that is performed after the data acquisition unit 100 completes the acquisition of data from the scan area 39 (B-scans repeated m times over each of the scan positions Y1 to Yn in the Y-direction) and the image generation unit 33 generates B-scan images from all the acquired data.

Figure 7:
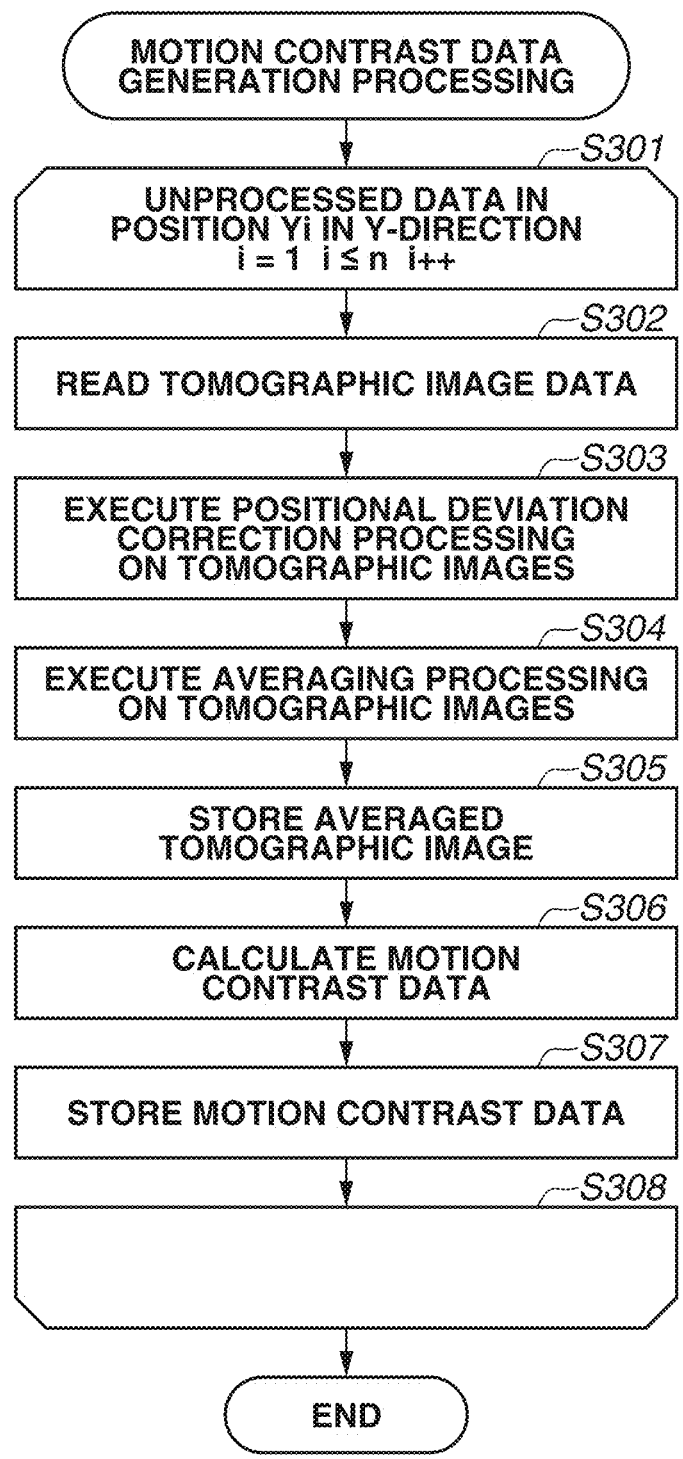
FIG. 7 is a flow chart illustrating an example of a process of generating motion contrast data.

In step S201, the OCTA image generation unit 35 generates motion contrast data (motion contrast value). Details of the generation of motion contrast data in step S201 will be described below with reference to FIG. 7. FIG. 7 is a flow chart illustrating an example of the generation of motion contrast data.

In step S301, the OCTA image generation unit 35 defines an index i of the position Yi in the Y-direction. In this way, steps S302 to S307 are performed with respect to every of the positions Y1 to Yn in the Y-direction.

In step S302, the OCTA image generation unit 35 reads from the storage unit 34 m pieces of B-scan images corresponding to the position Yi in the Y-direction.

In step S303, the OCTA image generation unit 35 performs positional deviation correction on the m pieces of B-scan images read in step S302. The positional deviation correction is performed because it is desirable to compare the B-scan images separated in time over the same position in the generation of motion contrast data. The positional deviation correction is performed, for example, to maximize the correlation between the B-scan images. As to the method for the positional deviation correction, any other known method can be used. The positional deviation correction is not necessary in a case in which the subject is not a moving object such as the eye-to-be-examined Er or a case in which tracking performance is high.

In step S304, the OCTA image generation unit 35 performs averaging processing on each pixel of the m pieces of B-scan images having undergone the positional deviation correction. Consequently, a single averaged B-scan image (hereinafter, also referred to as "averaged image") is acquired from the m pieces of B-scan images.

In step S305, the OCTA image generation unit 35 stores the single averaged B-scan image in the storage unit 34. Steps S304 and S305 do not have to be executed after step S303 and only need to be executed prior to the execution of processing that uses the averaged image.

In step S306, the OCTA image generation unit 35 calculates motion contrast data using the m pieces of B-scan images having undergone the positional deviation correction in step S303. The motion contrast data is acquired by calculating a variance value of each pixel of the m pieces of B-scan images having undergone the positional deviation correction in step S303. Specifically, the variance values are an example of the motion contrast value. There are various methods of calculating motion contrast data, and the motion contrast data can be calculated by a method other than the method used in the present exemplary embodiment. For example, the motion contrast data can be calculated by calculating a phase difference and/or a vector difference between the complex OCT signals that have undergone the Fourier transform performed by the image generation unit 33 and are to undergo the absolute value calculation. In other words, the motion contrast value is not limited to the above-described variance value and can be any value by which a portion with a change between images and a portion without a change between the images are distinguishable.

In step S307, the OCTA image generation unit 35 stores in the storage unit 34 the motion contrast data acquired in step S306.

In step S308, if steps S302 to S307 are performed on every one of the positions Y1 to Yn in the Y-direction, the motion contrast data generation processing is ended.

In step S201 including steps S301 to S308 described above, the OCTA image generation unit 35 acquires motion contrast data on each of the positions Y1 to Yn in the Y-direction.

Next, in step S202, the OCTA image generation unit executes segmentation. As used herein, the term "segmentation" refers to a process including the detection of retinal boundaries (layer boundaries) from an image.

In the segmentation, first, the OCTA image generation unit 35 reads from the storage unit 34 the averaged B-scan images stored in step S305. The averaged B-scan images are stored for the respective positions Y1 to Yn in the Y-direction, and the averaged B-scan images of all the positions in the Y-direction are read. After the reading is completed, the OCTA image generation unit 35 calculates the positions of boundaries in the cross section with respect to each of the B-scan images. Specifically, the positions of boundaries of the nerve fiber layer, the ganglion cell layer, the retinal pigment epithelium, etc. in the cross section are calculated. The OCTA image generation unit 35 performs edge extraction processing in the Z-direction on the B-scan images and analyzes the extracted edge profiles to obtain the positions of boundaries in the cross section. After the boundary positions in the cross sections in the B-scan images are obtained, the OCTA image generation unit 35 stores in the storage unit 34 data indicating the obtained boundary positions. Alternatively, each time a boundary position is detected, data indicating the detected boundary position can be stored in the storage unit 34. Further, while the boundary positions are detected from the averaged B-scan images in the above-described example, the boundary positions can be detected from the B-scan images that have not undergone the averaging processing.

Figure 8:
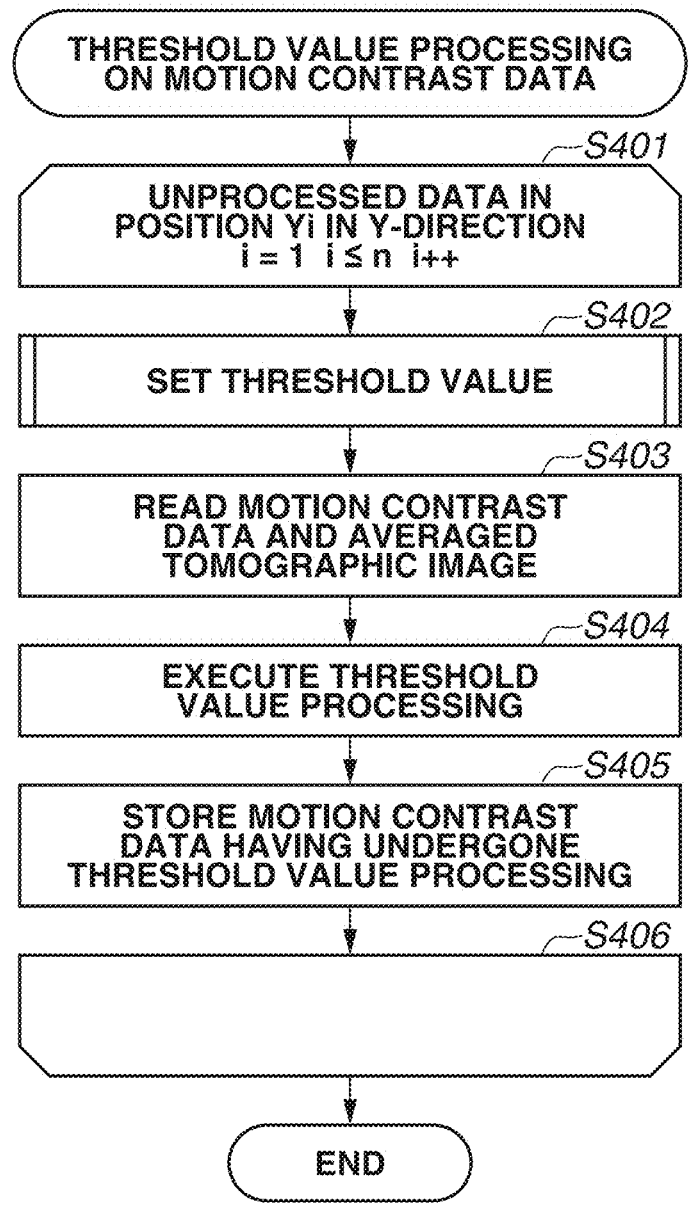
FIG. 8 is a flow chart illustrating an example of threshold value processing performed on motion contrast data.

Next, in step S203, the OCTA image generation unit 35 performs threshold value processing on the motion contrast data. Details of the threshold value processing performed on the motion contrast data in step S203 will be described below with reference to FIG. 8. FIG. 8 is a flow chart illustrating an example of the threshold value processing performed on the motion contrast data. The threshold value processing on the motion contrast data in FIG. 8 includes steps S401 to S406.

In step S401, the OCTA image generation unit 35 defines the index i in the position Yi in the Y-direction. In this way, steps S402 to S405 are repeated with respect to each of the positions Y1 to Yn in the Y-direction.

Figure 9:
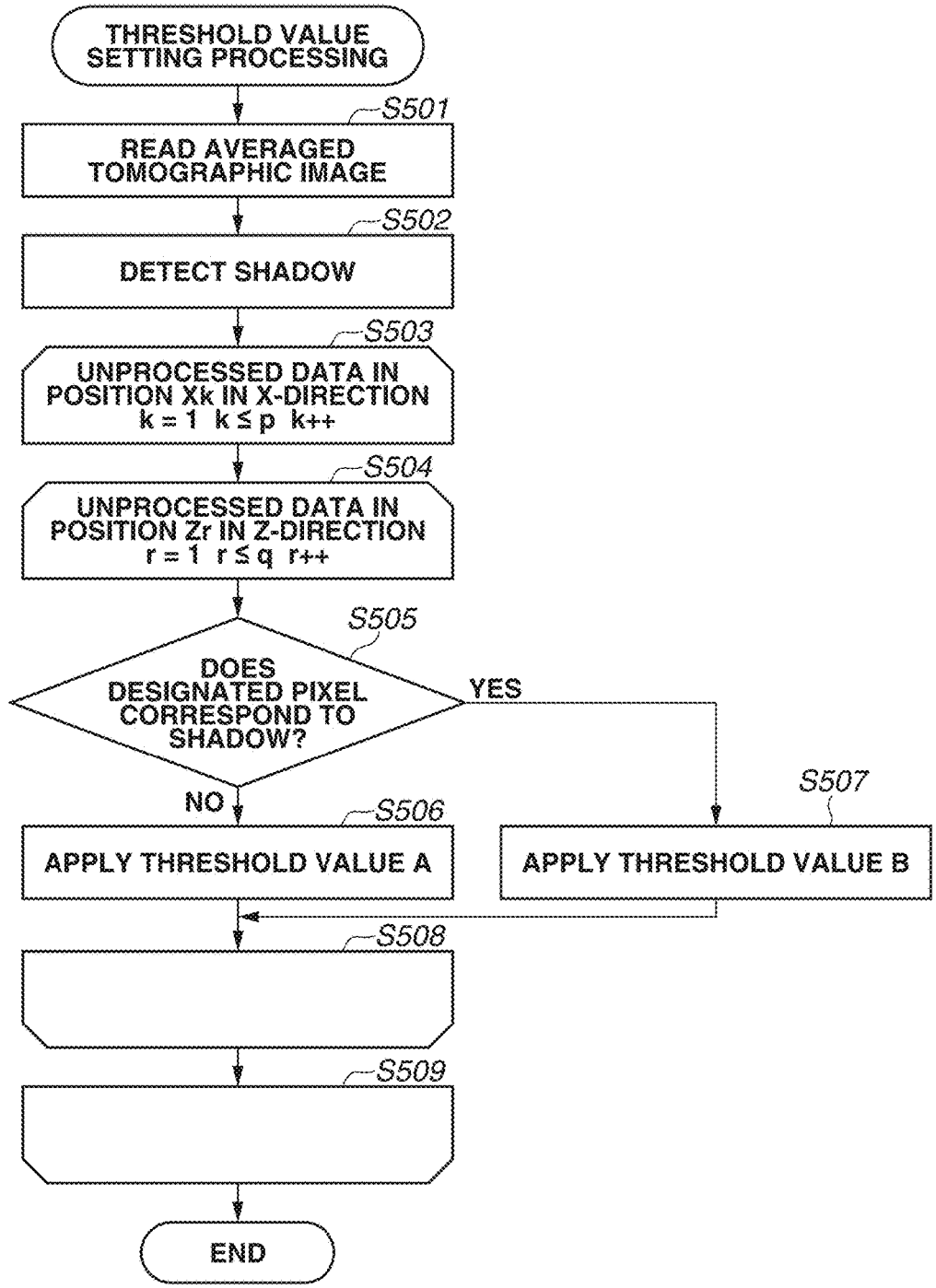
FIG. 9 is a flow chart illustrating an example of a threshold value setting process.

In step S402, the OCTA image generation unit 35 sets a threshold value. The threshold value set in step S402 is used in the threshold value processing on the motion contrast data which is performed in step S404. Details of step S402 will be described below with reference to FIG. 9. FIG. 9 is a flow chart illustrating an example of a threshold value setting process.

First, in step S501, the OCTA image generation unit 35 reads from the storage unit 34 the averaged B-scan image corresponding to the position Yi in the Y-direction which is stored in step S305.

Next, in step S502, the OCTA image generation unit 35 detects a shadow from the averaged B-scan image read in step S501. Then, the OCTA image generation unit 35 stores in the storage unit 34 data indicating the position of the detected shadow. As described above, the shadow is cast over the cross section which exists behind the shielding object viewed from the incident direction of the measurement light, and the position of the cast shadow in the Z-direction varies depending on the position of the shielding object in the Z-direction in the eye-to-be-examined Er. Thus, in step S502, the position of the cast shadow in the X-direction and the position from and behind which the shadow is cast in the Z-direction when viewed from the incident direction of the measurement light are detected using the averaged B-scan image read in step S501.

While two examples of a shadow detection method will be described below in the present exemplary embodiment, any other method by which a shadow is detectable can be used.

The first example is a method of detecting a shadow from luminance values of the B-scan images. In this method, first, the OCTA image generation unit 35 detects the position of a cast shadow in the X-direction. The OCTA image generation unit 35 divides the B-scan images into A-scan units and calculates the sum of all pixel values for each of the divided A-scan. A shadow is observed with a lower luminance than those of portions with no shadow, so the position of the shadow in the X-direction can be detected by detecting a position in the X-direction with a numerical value of the calculated sum that is equal to or smaller than a predetermined value. The above-described processing is not capable of detecting the position from and behind which the shadow is cast in the Z-direction, so the OCTA image generation unit 35 next detects the position in the Z-direction from and behind which the shadow is cast. The OCTA image generation unit 35 compares the pixel values of the A-scan of the position in the X-direction in which the shadow is detected to the pixel values of the A-scan of a nearby position in the X-direction in which no shadow is detected, with respect to the same position in the Z-direction. The position in the Z-direction in which the pixel value of the A-scan of the position in the X-direction in which the shadow is detected is lower than the pixel value of the A-scan of the nearby position in the X-direction in which no shadow is detected is detected to detect the position in the Z-direction from and behind which the shadow is cast. Examples of the nearby position in the X-direction in which no shadow is detected include the nearest position in the X-direction to the position in the X-direction in which the shadow is detected.

The second example is a method of detecting a shadow using the B-scan images and the segmentation result acquired in step S202. In this method, the OCTA image generation unit 35 first divides the B-scan images into layers using the segmentation result. Next, the OCTA image generation unit 35 extracts data of each layer sequentially in the incident direction of the measurement light from the vitreous body, i.e., the nerve fiber layer, the ganglion cell layer, and the inner plexiform layer, and divides the extracted data into A-scan units to calculate the sum of all pixel values for each of the divided A-scans. Since a shadow is observed with a lower luminance than those of portions with no shadow, the OCTA image generation unit 35 detects a position in the X-direction with a numerical value of the calculated sum that is equal to or smaller than a predetermined value. The OCTA image generation unit 35 performs the above-described processing with respect to each layer to detect the position of the cast shadow in the X-direction and the layer in the Z-direction from and behind which the shadow is cast. In a case in which a low luminance is detected from all the layers from the nerve fiber layer to the choroid, the OCTA image generation unit 35 detects a shadow caused by vitreous body opaque or lens opaque. Further, in a case in which a low luminance is detected from and behind any of the layers from the ganglion cell layer to the boundary between the inner nuclear layer and the outer plexiform layer when viewed from the incident direction of the measurement light, the OCTA image generation unit 35 detects a shadow caused by a retinal blood vessel. Specifically, a shadow is determined as being detected if a low luminance is detected from a layer and all layers located behind the layer when viewed from the incident direction of the measurement light.

Alternatively, the shadow extraction can be performed on the B-scan images that have not undergone the averaging processing. Alternatively, the OCTA image generation unit 35 reads at least one B-scan image from each of the positions Y1 to Yn in the Y-direction and generates an en-face image using the segmentation data acquired in step S202. Then, the OCTA image generation unit 35 detects a shadow from the en-face image. As used herein, the term "en-face image" refers to an image generated two-dimensionally in the XY-directions by determining a representative value of each A-scan from the data of a layer that is extracted by the segmentation. Pixels of the en-face image with a numerical value that is equal to or smaller than a predetermined value correspond to a shadow, so the position of a cast shadow in the XY-directions and the position in the Z-direction from and behind which the shadow is cast when viewed from the incident direction of the measurement light are detectable by sequentially performing the detection on the respective layers. Specifically, the OCTA image generation unit 35 corresponds to an example of an identification unit configured to identify a shadow region in at least one of a plurality of pieces of tomographic data.

Next, in steps S503 and S504, the OCTA image generation unit 35 defines an index k of the position Xk in the X-direction and an index r of the position Zr in the Z-direction. In this way, steps S505, S506, and S507 are performed on all the pixel positions of the B-scan images with respect to the positions X1 to Xp in the X-direction and the positions Z1 to Zq in the Z-direction.

Next, in step S505, the OCTA image generation unit 35 judges whether the pixels of the B-scan images of the positions (Xk, Zr) designated in steps S503 and S504 correspond to the shadow detected in step S502.

In step S505, if the OCTA image generation unit 35 judges that the pixels of the B-scan images do not correspond to the shadow (NO in step S505), then in step S506, the OCTA image generation unit 35 applies a threshold value A to the threshold value processing. On the other hand, if the OCTA image generation unit 35 judges that the pixels of the B-scan image correspond to the shadow (YES in step S505), then in step S507, the OCTA image generation unit 35 applies to the threshold value processing a threshold value B which is different from the threshold value A. Specifically, the OCTA image generation unit 35 corresponds to an example of a determination unit configured to determine, in a case where a shadow region is identified by the identification unit, a value different from a threshold value to which a signal intensity value corresponding to a region other than the shadow region is compared, as a threshold value to which a signal intensity value corresponding to the shadow region is compared. In a case where no shadow region is identified by the identification unit, the same value (threshold value A) is determined as threshold values to which signal intensity values of a plurality of positions in the same depth position or in the same layer in the tomographic data are respectively compared.

The threshold values A and B are used in step S404 described below. The smaller the threshold values A and B are, the higher the detection sensitivity of motion contrast data becomes, and noise components are increased. On the other hand, the larger the threshold values A and B are, the lower the detection sensitivity of motion contrast data becomes, and noise components are decreased.

The setting value of the threshold value A is, for example, a value obtained by adding 2σ to the mean value of luminance values of a portion other than a portion in which a subject is displayed in the B-scan image generated by the image generation unit 33, i.e., a portion in which only random noise is displayed. As used herein, the symbol "σ" refers to the standard deviation. Further, the setting value of the threshold value B is a value obtained by multiplying the setting value of the threshold value A by a coefficient α. Specifically, the OCTA image generation unit 35 determines based on the threshold value to which the signal intensity value corresponding to the region other than the shadow region is compared the threshold value to which the signal intensity value corresponding to the shadow region is compared. The coefficient α is a coefficient for correcting a decrease in luminance of a tomographic image that is caused by a shadow cast by a shielding object. The coefficient α is set to, for example, a fixed value that is larger than zero and smaller than one. Specifically, a threshold value to be applied differs depending on whether a pixel corresponds to a shadow. The threshold value B corresponding to a shadow is set smaller than the threshold value A corresponding to the case in which a pixel does not correspond to a shadow. Specifically, the threshold value to which a signal intensity value corresponding to a shadow region is compared is smaller than the threshold value to which a signal intensity value corresponding to a region other than the shadow region is compared. According to the conventional methods, steps S505 and S507 are not performed and the threshold values are set to a fixed value (threshold value A) regardless of whether a pixel corresponds to a shadow.

Further, while the threshold value B is described as a value determined based on the threshold value A and the coefficient α, the threshold value B does not have to be determined based on the threshold value A because the threshold value B only needs to be a value for correcting a decrease in luminance of a tomographic image that is caused by a shadow. Specifically, the threshold value B only needs to be smaller than the threshold value A, and the method of determining the threshold value B is not limited to the example described above.

While the coefficient α is described as a fixed value, the coefficient α can be a function of the intensity of a shadow to set a small coefficient α with respect to a portion with a strong shadow or a large coefficient α with respect to a portion with a weak shadow. Specifically, smaller coefficients α are set with respect to stronger shadows (smaller signal intensity values). As described above, the OCTA image generation unit 35 determines according to the signal intensity value corresponding to the shadow region the threshold value to which the signal intensity value corresponding to the shadow region. Specifically, the OCTA image generation unit 35 sets the threshold value to which the signal intensity value corresponding to the shadow region is compared such that the smaller the signal intensity value corresponding to the shadow region is, the smaller the threshold value is set. While the coefficient α is multiplied in the above-described example, the threshold value to which the signal intensity value corresponding to the shadow region can be set by subtracting a predetermined coefficient from the threshold value A or by dividing the threshold value A by a predetermined coefficient such that the smaller the signal intensity value corresponding to the shadow region is, the smaller the threshold value is set.

In this way, an appropriate value of the coefficient α is set with respect to each shadow in the eye-to-be-examined data acquired by the scans over the scan area 39.

For example, in the case of a shadow cast by a retinal blood vessel being a shielding object, if the blood vessel is thick in the Z-direction, a strong shadow is cast to cause a significant decrease in luminance of the tomographic image of the shadow portion. On the other hand, if the blood vessel is thin in the Z-direction, a weak shadow is cast to cause a less significant decrease in luminance of the tomographic image of the shadow portion. Thus, setting the coefficient α as a function of a signal intensity value of a shadow portion as described above enables the threshold value to be set as appropriate.

While the intensity of a shadow is described above as a decrease in luminance of a tomographic image, anything other than a decrease in luminance of a tomographic image that indicates the intensity of a shadow can be used to bring a consequence that the coefficient α is a function of the intensity of a shadow.

In steps S508 and S509, if steps S505 to S507 are performed on every one of the pixel positions of the B-scan images with respect to the positions X1 to Xp in the X-direction and the positions Z1 to Zq in the Z-direction, the processing is ended.

In step S402 including steps S501 to S509, the OCTA image generation unit 35 sets a threshold value with respect to each pixel of the B-scan images of the position Yi in the Y-direction with the shadow taken into consideration. Specifically, the OCTA image generation unit sets a threshold value as appropriate to each pixel instead of setting a uniform threshold value.

In step S403, the OCTA image generation unit 35 reads from the storage unit 34 the motion contrast data stored in the storage unit 34 in step S307 and corresponding to the position Yi in the Y-direction and the averaged B-scan image stored in step S305 and corresponding to the position Yi in the Y-direction.

In step S404, the OCTA image generation unit 35 performs threshold value processing on the motion contrast data. Specifically, the OCTA image generation unit 35 compares for each pixel a pixel value (signal intensity value) of the averaged B-scan image to the threshold value set in step S402, and if the pixel value of the averaged B-scan image is equal to the threshold value or less, the OCTA image generation unit 35 sets the motion contrast data corresponding to the pixel to zero.

On the other hand, if the pixel value of the averaged B-scan image is more than the threshold value, the value of the motion contrast data corresponding to the pixel is maintained. The value of the motion contrast data can be a value near zero and does not have to be exactly zero. Alternatively, the pixel value of the B-scan image that has not undergone the averaging processing can be compared to the threshold value. Specifically, the OCTA image generation unit 35 corresponds to an example of a comparison unit configured to compare the threshold value to a signal intensity value acquired from at least one of a plurality of pieces of tomographic data. Further, the OCTA image generation unit 35 corresponds to an example of a second acquisition unit configured to acquire a motion contrast value from a result of the comparison performed by the comparison unit and the plurality of pieces of tomographic data.

In step S405, the OCTA image generation unit 35 stores in the storage unit 34 the motion contrast data having undergone the threshold value processing in step S404.

In step S406, if steps S402 to S405 are performed on every one of the positions Y1 to Yn in the Y-direction, the threshold value processing is ended.

In step S203 including steps S401 to S406 described above, the OCTA image generation unit 35 performs the threshold value processing using the threshold value that is determined with the shadow taken into consideration.

Next, in step S204, the OCTA image generation unit 35 generates an OCTA image. Specifically, first, the OCTA image generation unit 35 reads from the storage unit 34 the boundary positions of the layers acquired by the segmentation in step S202. Next, in step S203, the OCTA image generation unit 35 extracts data of a layer from the motion contrast data having undergone the threshold value processing using the boundary positions of the layers acquired by the segmentation. Then, the OCTA image generation unit 35 determines a representative value of the A-scans with respect to the motion contrast data of the layer. The representative value can be any value such as a mean value, maximum value, or median value. The OCTA image generation unit 35 generates the representative value two-dimensionally in the XY-directions to generate a two-dimensional OCTA image. Specifically, the OCTA image generation unit 35 corresponds to an example of a generation unit configured to generate a motion contrast image based on the motion contrast value acquired by the second acquisition unit. The OCTA image generation unit 35 stores the two-dimensional OCTA image in the storage unit 34 and outputs the two-dimensional OCTA image (hereinafter, also referred to simply as "OCTA image") to the display unit 102 to display the OCTA image on the display unit 102.

Figure 10A:
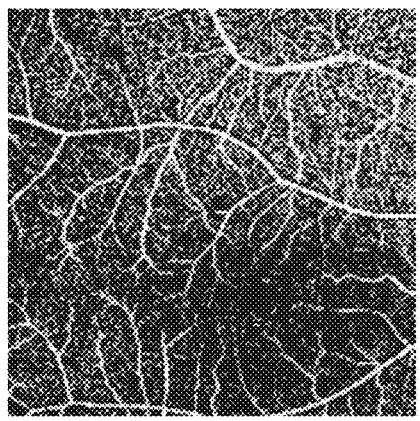
FIGS. 10A and 10B each illustrate an example of an OCTA image to which an exemplary embodiment of the present invention is applied, and FIGS. 10C and 10D each illustrate an example of an OCTA image to which a conventional technique is applied.
Figure 10C:
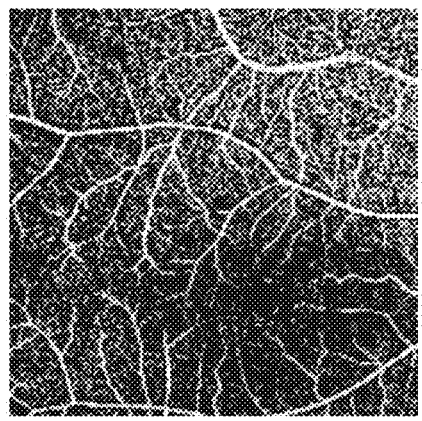
Figure 10B:
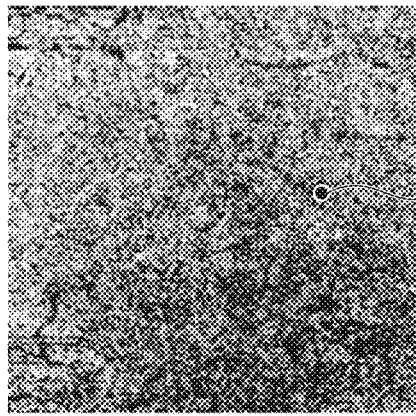

FIGS. 10A to 10D each illustrate an example of the two-dimensional OCTA image generated in step S204 or a two-dimensional OCTA image generated by a conventional method in which the threshold value is fixed. FIGS. 10A and 10B each illustrate an OCTA image generated according to the present exemplary embodiment, and FIGS. 10C and 10D each illustrate an OCTA image generated according to a conventional method. In the case of the conventional method, the threshold value set in step S402 is a fixed value (threshold value A) determined without considering as to whether there is a shadow.

Figure 10D:
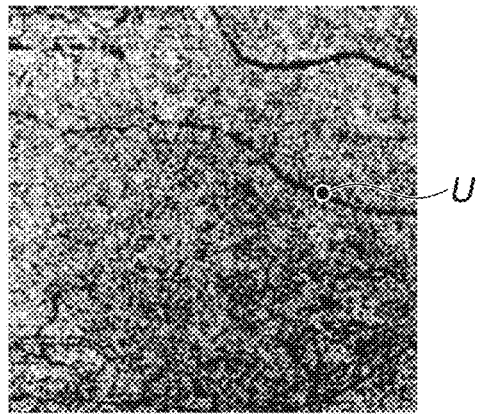

Further, FIGS. 10A and 10C illustrate OCTA images of the ganglion cell layer, and the existence of the retinal blood vessel is observed. FIGS. 10B and 10D illustrate OCTA images of the choriocapillaris.

First, as to the OCTA images of the ganglion cell layer in FIGS. 10A and 10C, the OCTA images are exactly the same image. Since there is no shadow in the ganglion cell layer, only the threshold value A is selected in step S505, so the OCTA image in FIG. 10A which is generated according to the present exemplary embodiment is the same as the image in FIG. 10C which is generated according to a conventional method.

On the other hand, as to the OCTA images of the choriocapillaris in FIGS. 10B and 10D, an artifact is found in a point U in the OCTA image in FIG. 10D which is generated by the conventional method. This artifact corresponds to the blood vessel in FIG. 10C. This is because a shadow cast by the retinal blood vessel being a shielding object exists over the choriocapillaris. The pixel values of the B-scan image of the shadow portion exhibit low luminance, so the motion contrast signal is set to zero by the threshold value processing. Consequently, an artifact is generated in the point U in FIG. 10D. On the other hand, in the OCTA image in FIG. 10B which is generated according to the present exemplary embodiment, the artifact in a point S located in the same area as the point U in FIG. 10D is reduced. The reason is as follows. According to the present exemplary embodiment, the threshold value set in step S402 is lower than the threshold value A with the shadow taken into consideration, so even if the pixel values of the B-scan image exhibit low luminance as in the shadow portion, the motion contrast signal is not set to zero by the threshold value processing, and the value is maintained. In other words, an appropriate OCTA image is obtainable from the shadow region.

While the present exemplary embodiment reduces artifacts by setting the threshold value B, which is smaller than the threshold value A, with respect to a portion corresponding to a shadow, the present exemplary embodiment may partially increasenoise components, but the threshold value A, which is a conventional setting value for reducing noise components, is set with respect to a portion other than the portion corresponding to a shadow, so OCTA images in which noise is overall not prominent are provided.

While spectral-domain OCT (SD-OCT) is described as an example in the present exemplary embodiment described above, time-domain OCT or swept-source OCT (SS-OCT) can be employed.

Further, while the OCTA image generation unit 35 uses the threshold value B with respect to the pixels corresponding to a shadow in the present exemplary embodiment described above, the threshold value B can be applied to all the pixels of the A-scan images including the pixels corresponding to a shadow. Specifically, the OCTA image generation unit 35 determines, as a threshold value to which a signal intensity of A-scan data including the shadow region is compared, the threshold value to which the signal intensity value corresponding to the shadow region is compared, regardless of whether the signal intensity value corresponds to the shadow region. Even in this way, appropriate OCTA images are obtainable from the shadow region.

Figure 11:
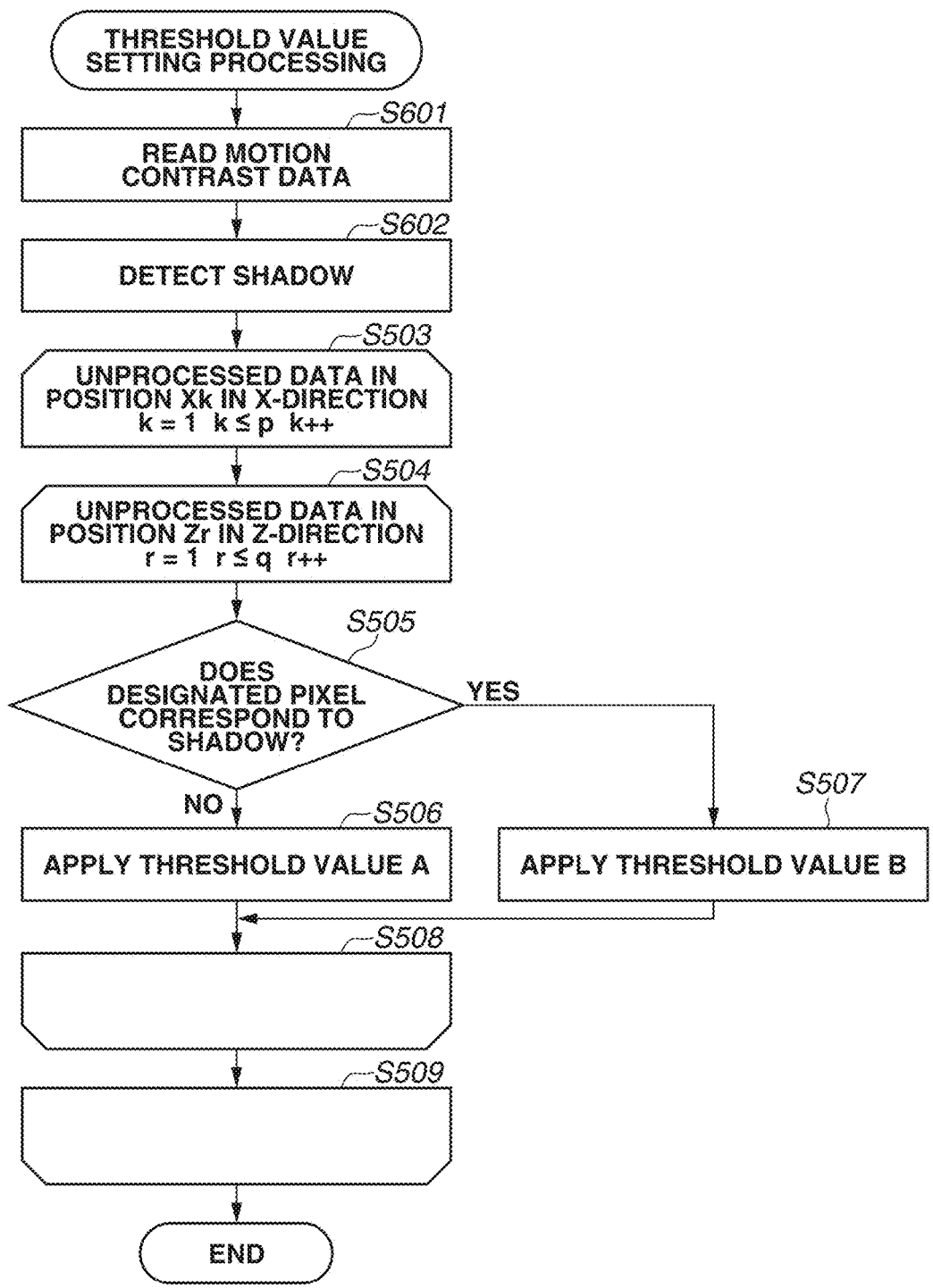
FIG. 11 is a flow chart illustrating an example of a threshold value setting process according to a second exemplary embodiment.

The configuration of an optical coherence tomographic imaging apparatus according to a second exemplary embodiment is similar to the configurations in FIGS. 1 to 3 according to the first exemplary embodiment. As to the processes performed by the OCTA image generation unit 35, the flow charts in FIGS. 6 to 8 used in the first exemplary embodiment are used in the second exemplary embodiment. Further, the flow chart in FIG. 9 according to the first exemplary embodiment is replaced by a flow chart in FIG. 11 in the second exemplary embodiment, and steps S501 and S502 in the first exemplary embodiment are replaced by steps S601 and 602 in the second exemplary embodiment. In the flow chart in FIG. 11, steps that are similar to those in the first exemplary embodiment are given the same reference numerals. The methods of observing and capturing images of the eye-to-be-examined Er are similar to those in the first exemplary embodiment, so description of the methods is omitted.

First, in steps S201 and S202, the OCTA image generation unit 35 generates motion contrast data with respect to each of the positions Y1 to Yn in the Y-direction and performs segmentation as in the first exemplary embodiment.

Next, in step S203, the OCTA image generation unit 35 performs threshold value processing on the motion contrast data. Step S203 includes steps S401 to S406. First, in step S401, the OCTA image generation unit 35 defines the index i of the position Yi in the Y-direction. Next, in step S402, the OCTA image generation unit 35 sets a threshold value. The threshold value setting process performed in step S402 is illustrated in the flow chart in FIG. 11. Step S402 includes steps S601 and S602 and steps S503 to S509.

In step S601, the OCTA image generation unit 35 reads from the storage unit 34 the motion contrast data stored in the storage unit 34 in step S307 and corresponding to the position Yi in the Y-direction.

In step S602, the OCTA image generation unit 35 detects the position of a cast shadow in the X-direction and the position in the Z-direction from and behind which the shadow is cast when viewed from the incident direction of the measurement light, using the motion contrast data read in step S601. While a shadow is detected from the B-scan images in the first exemplary embodiment, a shadow is detected from the motion contrast signal in the second exemplary embodiment.

As described above in the first exemplary embodiment, the motion contrast data acquired in step S201 indicates the position of the blood vessel portion, and a shadow is cast in a position behind the blood vessel portion. Thus, in step S602, the OCTA image generation unit 35 searches for and identifies a pixel with a numerical value that is not smaller than a predetermined value in the motion contrast data along the incident direction of the measurement light, and pixels located behind the identified position are determined as the position of the cast shadow. The OCTA image generation unit 35 performs the foregoing processing with respect to each A-scan to detect the position of the cast shadow in the X-direction and the position in the Z-direction from and behind which the shadow is cast when viewed from the incident direction of the measurement light. In other words, the OCTA image generation unit 35 identifies a shadow region based on the motion contrast values acquired from a plurality of pieces of tomographic data.

Next, in steps S503 to S509, the OCTA image generation unit 35 sets with respect to each pixel of the B-scan image of the position Yi in the Y-direction a threshold value with the shadow taken into consideration. This is similar to the processing in the first exemplary embodiment, so description thereof is omitted.

After the threshold values are set in step S402 described above, steps S403 to S406 are performed as in the first exemplary embodiment. In this way, the threshold value processing on the motion contrast data in step S203 is performed.

Lastly, in step S204, an OCTA image is generated as in the first exemplary embodiment.

The second exemplary embodiment is different from the first exemplary embodiment in that the shadow detection is performed using the motion contrast data, but the threshold value set in step S402 is a small value with the shadow taken into consideration as in the first exemplary embodiment. Thus, the OCTA image acquired in step S204 in the second exemplary embodiment is advantageous as in the first exemplary embodiment.

The first and second exemplary embodiments can be combined. For example, the OCTA image generation unit 35 can determine common pixels of the shadow detected in step S502 and the shadow detected in step S602 as pixels for which the threshold value is to be changed. This can improve the accuracy of shadow detection.

The configuration of an optical coherence tomographic imaging apparatus according to a third exemplary embodiment is similar to the configurations illustrated in FIGS. 1 to 3. The processes performed by the OCTA image generation unit 35 are similar to those in the first exemplary embodiment, and the flow charts in FIGS. 6 to 9 are also used in the third exemplary embodiment. While the process up to the display of the OCTA image generated in steps S201 to S204 on the display unit 102 is described in the first exemplary embodiment, a case in which, for example, a user having seen the OCTA image displayed in the first exemplary embodiment changes the threshold values with respect to the positions on the XY-plane individually using a graphical user interface (GUI), etc. will be described in the third exemplary embodiment.

Figure 12:
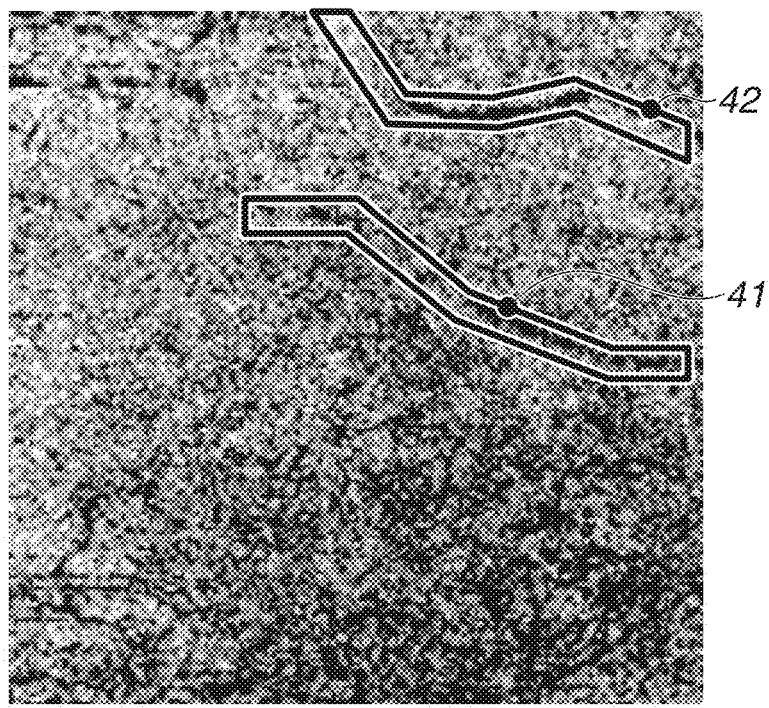
FIG. 12 illustrates an example of an OCTA image including a shadow region.

After the OCTA image generated in steps S201 to S204 is displayed on the display unit 102, the user checks the OCTA image and judges whether there is an artifact caused by a shadow. If the user judges that there is an artifact caused by a shadow, the user selects a region in which the artifact is present on the XY-plane using an operation member (not illustrated) such as a mouse. The OCTA image generation unit 35 receives the region selection by the user. FIG. 12 illustrates an example of the OCTA image of the choriocapillaris including an artifact caused by a shadow. Further, a region 41 specified in real lines in FIG. 12 indicates the region selected by the user and including the artifact caused by the shadow.

After the user selects the region 41 including the artifact, the user designates the setting value of the threshold value B (or the coefficient α) of the region 41 using the operation member (not illustrated). The OCTA image generation unit 35 receives a change to the threshold value B which is made by the user. Specifically, the OCTA image generation unit 35 corresponds to an example of a reception unit configured to receive a change made by the user to the threshold value to which the signal intensity value corresponding to the shadow region is compared. The method of setting the threshold value B (or the coefficient α) by the user can be, for example, a method using a text box, slide bar, etc. The OCTA image generation unit 35 can display a text box or slide bar on the display unit 102 in response to the reception of the selection of the region 41. Further, besides the methods using a GUI, such as a text box or slide bar, for example, a method in which the threshold value is changed in response to a rotation of a mouse wheel can be used.

After the OCTA image generation unit 35 receives a change to the threshold value B, the OCTA image generation unit 35 reads from the storage unit 34 the motion contrast data corresponding to the position of the designated region 41. Then, the OCTA image generation unit 35 executes the threshold value processing on the motion contrast data using the threshold value B set by the user, and displays again on the display unit 102 the OCTA image having undergone the threshold value processing. In other words, the OCTA image generation unit 35 reflects a result of the change to the threshold value B in real time to the OCTA image. Specifically, each time the reception unit receives a change to the threshold value to which the signal intensity value corresponding to the shadow region is compared, the second acquisition unit acquires a motion contrast value and the generation unit generates a motion contrast image. The foregoing processing is repeated until, for example, the user judges that there is no longer a region including an artifact.

Further, in a case in which a region including an artifact caused by a shadow is different from the region 41, the user selects a new region 42 including the artifact on the XY-plane using the operation member (not illustrated) such as a mouse, and sets to the region 42 the threshold value B which is a different value from the threshold value B set to the region 41. For example, the OCTA image generation unit 35 displays a text box, etc. for the region 42 on the display unit 102 in addition to the text box, etc. for the region 41 in response to the reception of the selection of the region 42. As to the region 42, similarly, the OCTA image generation unit 35 performs threshold value processing on the motion contrast data corresponding to the position of the region 42 using the threshold value B set by the user, and displays on the display unit 102 the OCTA image having undergone the threshold value processing. The regions for which the threshold value B is to be changed is not limited to the two regions of the regions 41 and 42, and the threshold values of three or more regions or the threshold value of one region can be changed.

As described above, the user checks the artifact caused by the shadow in the OCTA image and manually sets an appropriate threshold value with respect to each position on the XY-plane, so the user can acquire without stress an OCTA image with a reduced artifact caused by a shadow.

While the OCTA image of the choriocapillaris is described in the present exemplary embodiment, the user can set a threshold value for each layer with respect to a region including an artifact caused by a shadow.

The third exemplary embodiment can be implemented independently of the first and second exemplary embodiments. Specifically, instead of automatically setting a threshold value as appropriate according to a shadow, the user can be authorized to change the threshold value as desired. Further, the third exemplary embodiment can be combined with the first exemplary embodiment and/or the second exemplary embodiment. In this case, if the user judges that an artifact remains although the threshold value is automatically set, the threshold value can be changed as desired by the user, so an OCTA image with image quality desired by the user is obtainable.

The configuration of an optical coherence tomographic imaging apparatus according to a fourth exemplary embodiment is similar to the configurations illustrated in FIGS. 1 to 3. The processes performed by the OCTA image generation unit 35 are similar to those in the first exemplary embodiment, and the flow charts in FIGS. 6 to 9 are also used in the fourth exemplary embodiment. While the case in which the threshold value A used in step S506 is a fixed value is described in the first exemplary embodiment, a case in which the threshold value A is not a fixed value will be described below in the fourth exemplary embodiment.

The threshold value A set as a fixed value in the first exemplary embodiment is a value obtained by adding $2\sigma$ ($\sigma$=standard deviation) to the mean value of portions where only random noise is displayed in the B-scan image, and this is based on the assumption that a random noise component in the B-scan image does not change in any position in the B-scan image. However, noise characteristics of interference data acquired from the line sensor 32 can differ between low-frequency and high-frequency components, so values of random noise components in the Fourier-transformed B-scan image can vary depending on the position in the Z-direction.

Thus, in the fourth exemplary embodiment, the image generation unit 33 acquires, for example, a B-scan image with no subject displayed. Then, the OCTA image generation unit 35 calculates along the X-direction the mean value and the standard deviation $\sigma$ of the positions in the Z-direction in the B-scan image with no subject displayed, and sets as the threshold value A the value obtained by adding $2\sigma$ ($\sigma$=standard deviation) to the mean value. In this way, the threshold value A is set with the noise characteristics taken into consideration that vary depending on the position in the Z-direction. Thus, for example, the threshold value A to which the pixel value of the same depth position or the same layer is compared is the same value when the shadow is not taken into consideration.

On the other hand, the threshold value B set in step S507 in the fourth exemplary embodiment is a value obtained by multiplying the set threshold value A by the coefficient $\alpha$ for correcting the influence of the shadow. The coefficient $\alpha$ to be multiplied can be a fixed value as in the first exemplary embodiment or a value that varies according to the intensity of the shadow. Accordingly, the OCTA image generation unit 35 determines, as the threshold value to which the signal intensity value corresponding to the shadow region is compared, a value different from a threshold value to which a signal intensity value corresponding to a region that is other than the shadow region and is in the same depth position or in the same layer as the shadow region is compared.

In this way, the threshold value is set as appropriate for the shadow and for the region other than the shadow, so an image with reduced artifacts is provided with respect to the portion including the shadow in the OCTA image while the OCTA image with great accuracy of blood vessel extraction is provided with respect to the portion other than the shadow.

While the threshold value B is described as a value determined based on the threshold value A and the coefficient $\alpha$, the threshold value B does not have to be determined based on the threshold value A because the threshold value B only needs to be a value for correcting a decrease in luminance of a tomographic image that is caused by a shadow.

While the threshold value A is set based on the noise characteristics that vary depending on the position in the Z-direction in the present exemplary embodiment, the threshold value A can be set based on, for example, the interference signal intensity that varies depending on the position of the Z-direction. Specifically, the threshold value A can be set such that the lower the interference signal intensity is, the lower the threshold value A is set.

Further, the fourth exemplary embodiment can be implemented in combination with at least one of the first to third exemplary embodiments.

While the example in which the threshold value is switched between the threshold values A and B according to whether a pixel corresponds to a shadow so that an artifact caused by the shadow is reduced is described in the first to fourth exemplary embodiments, the present invention is not limited to the exemplary embodiments described above.

In a fifth exemplary embodiment, an example will be described in which the luminance of a tomographic image is changed instead of switching the threshold value. Specifically, the OCTA image generation unit 35 changes the luminance of a tomographic image according to whether a pixel corresponds to a shadow, instead of switching the threshold value according to whether a pixel corresponds to a shadow.

The OCTA image generation unit 35, for example, increases a luminance value (signal intensity value) of a pixel that corresponds to a shadow while maintaining a luminance value (signal intensity value corresponding to a region other than the shadow region) of a pixel that does not correspond to the shadow. As to a method of increasing the luminance value, for example, an offset value is added to the pixel. An amount (offset amount) by which the luminance value is increased can be a uniform value or an amount according to the original luminance value. For example, the OCTA image generation unit 35 determines the amount by which the luminance value is increased such that the smaller the original luminance value is, the larger the amount is set.

According to the present exemplary embodiment, the threshold value B is not used, whereas the threshold value A is used. In other words, the threshold value to which the increased signal intensity is compared is the same value as a threshold value to which a signal intensity value corresponding to a region that is other than the shadow region and is in the same depth position or in the same layer as the shadow region is compared.

Further, a target of increasing the luminance value can be a pixel of the averaged B-scan image or a pixel of the B-scan image that has not undergone the averaging processing. Specifically, the OCTA image generation unit 35 corresponds to an example of a control unit configured to increase a signal intensity value corresponding to the shadow region and acquired from at least one of the plurality of pieces of tomographic data. Further, according to the present exemplary embodiment, the OCTA image generation unit 35 executes threshold value processing by comparing the increased signal intensity value to the threshold value.

According to the present exemplary embodiment, an appropriate OCTA image is obtainable from the shadow region.

The fifth exemplary embodiment can be implemented in combination with at least one of the first to fourth exemplary embodiments. For example, the threshold value A does not have to be a fixed value. Further, the threshold value can be switched and the luminance value can be changed as in the present exemplary embodiment.

Other Embodiments

Embodiment(s) of the present invention can also be realized by a computer of a system or apparatus that reads out and executes computer executable instructions (e.g., one or more programs) recorded on a storage medium (which may also be referred to more fully as a 'non-transitory computer-readable storage medium') to perform the functions of one or more of the above-described embodiment(s) and/or that includes one or more circuits (e.g., application specific integrated circuit (ASIC)) for performing the functions of one or more of the above-described embodiment(s), and by a method performed by the computer of the system or apparatus by, for example, reading out and executing the computer executable instructions from the storage medium to perform the functions of one or more of the above-described embodiment(s) and/or controlling the one or more circuits to perform the functions of one or more of the above-described embodiment(s). The computer may comprise one or more processors (e.g., central processing unit (CPU), micro processing unit (MPU)) and may include a network of separate computers or separate processors to read out and execute the computer executable instructions. The computer executable instructions may be provided to the computer, for example, from a network or the storage medium. The storage medium may include, for example, one or more of a hard disk, a random-access memory (RAM), a read only memory (ROM), a storage of distributed computing systems, an optical disk (such as a compact disc (CD), digital versatile disc (DVD), or Blu-ray Disc (BD)™), a flash memory device, a memory card, and the like.

While the present invention has been described with reference to exemplary embodiments, it is to be understood that the invention is not limited to the disclosed exemplary embodiments. The scope of the following claims is to be accorded the broadest interpretation so as to encompass all such modifications and equivalent structures and functions.

This application claims the benefit of Japanese Patent Application No. 2016-213422, filed Oct. 31, 2016, which is hereby incorporated by reference herein in its entirety.

What is claimed is:

1. An information processing apparatus comprising:
a memory storing a program; and
at least a processor, by executing the program, functions as:
a first acquisition unit configured to obtain a plurality of pieces of tomographic data each of which indicates a cross section of an eye fundus and is obtained using measurement light which is controlled so that a same position of the eye fundus is scanned;
an identification unit configured to identify a shadow region in at least one of the plurality of pieces of tomographic data;
a determination unit configured to determine, in a case where a shadow region is identified by the identification unit, a value as a second threshold value different from a first threshold value, wherein the first threshold value is compared to a signal intensity value corresponding to a region other than the shadow region, and the second threshold value is compared to a signal intensity value corresponding to the shadow region;
a comparison unit configured to compare the first threshold value or the second threshold value to a signal intensity value obtained from at least one of the plurality of pieces of tomographic data;
a second acquisition unit configured to obtain a motion contrast value using a result of the comparison performed by the comparison unit and the plurality of pieces of tomographic data; and
a generation unit configured to generate a motion contrast image based on the motion contrast value obtained by the second acquisition unit.

2. The information processing apparatus according to claim 1, wherein the threshold value to which the signal intensity value corresponding to the shadow region is compared is smaller than the threshold value to which the signal intensity value corresponding to the region other than the shadow region is compared.

3. The information processing apparatus according to claim 1, wherein the determination unit determines, according to the signal intensity value corresponding to the shadow region, the threshold value to which the signal intensity value corresponding to the shadow region is compared.

4. The information processing apparatus according to claim 3, wherein the determination unit sets the threshold value to which the signal intensity value corresponding to the shadow region is compared such that the smaller the signal intensity value corresponding to the shadow region is, the smaller the threshold value is set.

5. The information processing apparatus according to claim 1, wherein the determination unit determines, based on the threshold value to which the signal intensity value corresponding to the region other than the shadow region is compared, the threshold value to which the signal intensity value corresponding to the shadow region is compared.

6. The information processing apparatus according to claim 1, wherein the determination unit determines, as the threshold value to which the signal intensity value corresponding to the shadow region is compared, a value different from a threshold value to which a signal intensity value corresponding to a region that is other than the shadow region and is in the same depth position or in the same layer as the shadow region is compared.

7. The information processing apparatus according to claim 1, wherein the determination unit determines, as a threshold value to which a signal intensity of A-scan data including the shadow region is compared, the threshold value to which the signal intensity value corresponding to the shadow region is compared, regardless of whether the signal intensity value corresponds to the shadow region.

8. The information processing apparatus according to claim 1, wherein in a case where no shadow region is identified by the identification unit, the same value is determined by the determination unit as threshold values to which signal intensity values of a plurality of positions in the same depth position or in the same layer in the tomographic data are respectively compared.

9. The information processing apparatus according to claim 1, wherein the identification unit identifies the shadow region based on the motion contrast value obtained from the plurality of pieces of tomographic data.

10. The information processing apparatus according to claim 1, wherein the processor further function as a reception unit configured to receive a change made by a user to the threshold value to which the signal intensity value corresponding to the shadow region is compared,
wherein each time the reception unit receives a change to the threshold value to which the signal intensity value corresponding to the shadow region is compared, the second acquisition unit obtains a motion contrast value and the generation unit generates a motion contrast image.

11. An information processing method comprising:
obtaining a plurality of pieces of tomographic data each of which indicates a cross section of an eye fundus and is obtained using measurement light which is controlled so that a same position of the eye fundus is scanned;
identifying a first region having a signal intensity value lower than a signal intensity value corresponding to a second region different from the first region, the first region and the second region being included in at least one of the plurality of pieces of tomographic data;
determining a threshold value to which the signal intensity value corresponding to the first region is compared, the threshold value to which the signal intensity value corresponding to the first region is compared being smaller than a threshold value to which the signal intensity value corresponding to the second region is compared;
comparing the threshold value to a signal intensity value obtained from at least one of the plurality of pieces of tomographic data;
obtaining a motion contrast value using a result of the comparing and the plurality of pieces of tomographic data; and
generating a motion contrast image using the acquired motion contrast value.

12. A non-transitory storage medium not temporarily storing a program for causing a computer to execute each step in the information processing method according to claim 11.

13. An information processing apparatus comprising:
a memory for storing a program; and
at least a processor, by executing the program, function as:
a first acquisition unit configured to obtain a plurality of pieces of tomographic data each of which indicates a cross section of an eye fundus and is obtained using measurement light which is controlled so that a same position of the eye fundus is scanned;
an identification unit configured to identify a shadow region in at least one of the plurality of pieces of tomographic data;
a control unit configured to increase a signal intensity value corresponding to the shadow region and obtained from at least one of the plurality of pieces of tomographic data;
a comparison unit configured to compare a threshold value to the signal intensity value increased by the control unit;
a second acquisition unit configured to obtain a motion contrast value using a result of the comparison performed by the comparison unit and the plurality of pieces of tomographic data; and
a generation unit configured to generate a motion contrast image using the motion contrast value obtained by the second acquisition unit.

14. The information processing apparatus according to claim 13, wherein a signal intensity value corresponding to a region other than the shadow region is maintained.

15. The information processing apparatus according to claim 13, wherein the threshold value to which the signal intensity value increased by the control unit is compared is the same value as a threshold value to which a signal intensity value corresponding to a region that is other than the shadow region and is in the same depth position or in the same layer as the shadow region is compared.

16. An information processing apparatus comprising:
a memory for storing a program; and
at least a processor, by executing the program, function as:
a first acquisition unit configured to obtain a plurality of pieces of tomographic data each of which indicates a cross section of an eye fundus and is obtained using measurement light which is controlled so that a same position of the eye fundus is scanned;
an identification unit configured to identify a first region having a signal intensity value lower than a signal intensity value corresponding to a second region different from the first region, the first region and the second region being included in at least one of the plurality of pieces of tomographic data;
a determination unit configured to determine a threshold value to which the signal intensity value corresponding to the first region is compared, the threshold value to which the signal intensity value corresponding to the first region is compared being smaller than a threshold value to which the signal intensity value corresponding to the second region is compared;
a comparison unit configured to compare the threshold value to a signal intensity value obtained from at least one of the plurality of pieces of tomographic data;
a second acquisition unit configured to obtain a motion contrast value using a result of the comparison performed by the comparison unit and the plurality of pieces of tomographic data; and
a generation unit configured to generate a motion contrast image based on the motion contrast value obtained by the second acquisition unit.

17. The information processing apparatus according to claim 16, wherein the determination unit determines, according to the signal intensity value corresponding to the first region, the threshold value to which the signal intensity value corresponding to the first region is compared.

18. The information processing apparatus according to claim 17, wherein the determination unit sets the threshold value to which the signal intensity value corresponding to the first region is compared such that the smaller the signal intensity value corresponding to the first region is, the smaller the threshold value is set.

19. The information processing apparatus according to claim 16, wherein the determination unit determines, based on the threshold value to which the signal intensity value corresponding to the first region is compared, the threshold value to which the signal intensity value corresponding to the first region is compared.

20. The information processing apparatus according to claim 16, wherein the determination unit determines, as the threshold value to which the signal intensity value corresponding to the first region is compared, a value different from a threshold value to which a signal intensity value corresponding to a region corresponding to the first region and in a same depth position or in a same layer as the first region is compared.

21. The information processing apparatus according to claim 16, wherein the determination unit determines, as a threshold value to which a signal intensity of A-scan data including the first region is compared, the threshold value to which the signal intensity value corresponding to the first region is compared, regardless of whether the signal intensity value corresponds to a shadow region.

22. The information processing apparatus according to claim 16, wherein in a case where the first region is not identified by the identification unit, a same value is determined by the determination unit as threshold values to which signal intensity values of a plurality of positions in a same depth position or in a same layer in the tomographic data are respectively compared.

23. The information processing apparatus according to claim 16, wherein the identification unit identifies the first region based on the motion contrast value obtained from the plurality of pieces of tomographic data.

24. The information processing apparatus according to claim 16, wherein the process further functions as a reception unit configured to receive a change made by a user to the threshold value to which the signal intensity value corresponding to the first region is compared, wherein each time the reception unit receives a change to the threshold value to which the signal intensity value corresponding to the first region is compared, the second acquisition unit obtains a motion contrast value and the generation unit generates a motion contrast image.

25. The information processing apparatus according to claim 16, wherein the generation unit generates, as the motion contrast image, an en-face image of OCTA using the motion contrast value and data of an arbitrary layer of the eye fundus, the data being detected by the segmentation.

26. An optical coherence tomographic imaging apparatus having the information processing apparatus according to claim 16, the optical coherence tomographic imaging apparatus further comprises a scanning unit configured to scan the eye fundus with the measurement light, wherein the optical coherent tomographic imaging apparatus is structured such that an interference light is detected, the interference light being obtained by combining a return light and a reference light, the return light being from the eye fundus illuminated with the controlled measurement light.

27. An information processing apparatus comprising:
a memory for storing a program; and
at least a processor, by executing the program, function as:

a first acquisition unit configured to obtain a plurality of pieces of tomographic data each of which indicates a cross section of an eye fundus and is obtained using measurement light which is controlled so that a same position of the eye fundus is scanned;
an identification unit configured to identify a first region having a signal intensity value lower than a signal intensity value corresponding to a second region different from the first region, the first region and the second region being included in at least one of the plurality of pieces of tomographic data;
a control unit configured to increase the signal intensity value corresponding to the first region and obtained from at least one of the plurality of pieces of tomographic data;
a comparison unit configured to compare a threshold value to the signal intensity value increased by the control unit;
a second acquisition unit configured to obtain a motion contrast value using a result of the comparison performed by the comparison unit and the plurality of pieces of tomographic data; and
a generation unit configured to generate a motion contrast image using the motion contrast value obtained by the second acquisition unit.

28. The information processing apparatus according to claim 27, wherein the signal intensity value corresponding to the first region is maintained.

29. The information processing apparatus according to claim 27, wherein the threshold value to which the signal intensity value increased by the control unit is compared is a same value as a threshold value to which the signal intensity value corresponding to the first region and in a same depth position or in a same layer as the first region is compared.

30. The information processing apparatus according to claim 27, wherein the generation unit generates, as the motion contrast image, an en-face image of OCTA using the motion contrast value and data of an arbitrary layer of the eye fundus, the data being detected by the segmentation.

31. An optical coherence tomographic imaging apparatus having the information processing apparatus according to claim 27, the optical coherence tomographic imaging apparatus further comprises a scanning unit configured to scan the eye fundus with the measurement light, wherein the optical coherent tomographic imaging apparatus is structured such that an interference light is detected, the interference light being obtained by combining a return light and a reference light, the return light being from the eye fundus illuminated with the controlled measurement light.

32. An information processing method comprising:
obtaining a plurality of pieces of tomographic data each of which indicates a cross section of an eye fundus and is obtained using measurement light which is controlled so that a same position of the eye fundus is scanned;
identifying a first region having a signal intensity value lower than a signal intensity value corresponding to a second region different from the first region, the first region and the second region being included in at least one of the plurality of pieces of tomographic data;
increasing the signal intensity value corresponding to the first region and obtained from at least one of the plurality of pieces of tomographic data;
comparing a threshold value to the increased signal intensity value;

obtaining a motion contrast value using a result of the comparing and the plurality of pieces of tomographic data; and generating a motion contrast image using the obtained motion contrast value.

33. A non-transitory storage medium not temporarily storing a program for causing a computer to execute each step in the information processing method according to claim 32.

* * * * *